US012692321B2

(12) United States Patent

Karim et al.

(10) Patent No.: US 12,692,321 B2

(45) Date of Patent: *Jul. 28, 2026

(54) ANTIBODIES AND ANTIGEN BINDING FRAGMENTS AGAINST CD155 METHODS OF USE THEREOF

(71) Applicant: Tasrif Pharmaceutical, LLC, Farmingdale, NY (US)

(72) Inventors: Aftab S. Karim, Farmington, NY (US); Robert Holgate, Babraham (GB); Arron Hearn, Babraham (GB)

(73) Assignee: TASRIF PHARMACEUTICAL, LLC, Farmingdale, NY (US)

( * ) Notice: Subject to any disclaimer, the term of this patent is extended or adjusted under 35 U.S.C. 154(b) by 1298 days.

This patent is subject to a terminal disclaimer.

(21) Appl. No.: 17/407,527

(22) Filed: Aug. 20, 2021

(65) Prior Publication Data

US 2022/0056146 A1 Feb. 24, 2022

Related U.S. Application Data

(63) Continuation-in-part of application No. 16/365,330, filed on Mar. 26, 2019, now Pat. No. 11,098,130, which is a continuation of application No. 16/247,278, filed on Jan. 14, 2019, now abandoned, which is a continuation-in-part of application No. 15/227,339, filed on Aug. 3, 2016, now abandoned.

(60) Provisional application No. 62/200,506, filed on Aug. 3, 2015.

(51) Int. Cl.
*C07K 16/28* (2006.01)
*A61K 47/68* (2017.01)

(52) U.S. Cl.
CPC .... *C07K 16/2896* (2013.01); *A61K 47/68037* (2023.08); *A61K 47/6849* (2017.08); *C07K 2317/24* (2013.01); *C07K 2317/51* (2013.01); *C07K 2317/515* (2013.01); *C07K 2317/53* (2013.01); *C07K 2317/732* (2013.01); *C07K 2317/734* (2013.01)

(58) Field of Classification Search
CPC ............ C07K 16/2896; C07K 2317/24; C07K 2317/51; C07K 2317/515; C07K 2317/53; C07K 2317/732; C07K 2317/734; C07K 2317/77; C07K 2317/92; A61K 47/68037; A61K 47/6849
See application file for complete search history.

(56) References Cited

U.S. PATENT DOCUMENTS

| 11,098,130 B1 * | 8/2021 | Karim | A61K 31/495 |
| 2018/0185482 A1 * | 7/2018 | Sheng | A61K 39/0011 |

FOREIGN PATENT DOCUMENTS

| MA | 32713 B1 * | 10/2011 | A61P 35/02 |
| WO | WO-2017149538 A1 * | 9/2017 | A61P 37/02 |
| WO | WO-2018210898 A1 * | 11/2018 | A61K 35/00 |
| WO | WO-2018237157 A1 * | 12/2018 | A61K 31/495 |

OTHER PUBLICATIONS

Mariuzza RA et al. The structural basis of antigen-antibody recognition. Annu Rev Biophys Biophys Chem. 1987;16:139-59. (Year: 1987).*

Angal S, King DJ, Bodmer MW, Turner A, Lawson AD, Roberts G, Pedley B, Adair Jr. A single amino acid substitution abolishes the heterogeneity of chimeric mouse/human (IgG4) antibody. Mol Immunol. Jan. 1993;30(1): 105-8. (Year: 1993).*

Kaspar et al. The antibody-mediated targeted delivery of interleukin-15 and GM-CSF to the tumor neovasculature inhibits tumor growth and metastasis. Cancer Res. May 15, 2007;67(10):4940-8. (Year: 2007).*

Seth S., et al. Intranodal Interaction with Dendritic Cells Dynamically Regulates Surface Expression of the Co-stimulatory Receptor CD226 Protein on Murine T Cells. Journal of Biological Chemistry, 2011 vol. 286, Issue 45, pp. 39153-39163. (Year: 2011).*

Farrington, G.K., et al. (2014) A novel platform for engineering blood-brain barrier-crossing bispecific biologics. The FASEB Journal, 28: 4764-4778. (Year: 2014).*

* cited by examiner

*Primary Examiner* — Sean E Aeder
*Assistant Examiner* — Yie Chia Lee
(74) *Attorney, Agent, or Firm* — Lando & Anastasi, LLP

(57) ABSTRACT

A humanized antibody or antigen binding fragment that binds to the poliovirus receptor (PVR) can be utilized in the preparation of antibody drug conjugates (ADCs) to target nucleic acids, peptides and proteins, drugs and radiopharmaceuticals to cancer cells. These antibodies or antigen binding fragments can also be used for checkpoint blockade. The humanized antibody or antigen binding fragment of this invention can also modulate the PVR-DNAM-1 axis in order to upregulate DNAM 1 (CD226) expression on T cells or NK cells. The antibody or antigen binding fragment that bind to PVR can also be incorporated in CAR-T cells or CAR-NK cells. Bispecific antibodies can also be produced by incorporating the anti-CD155 antibodies or antigen binding fragments to engage T cells or NK cells to fight cancers that express CD155.

19 Claims, 8 Drawing Sheets

Specification includes a Sequence Listing.

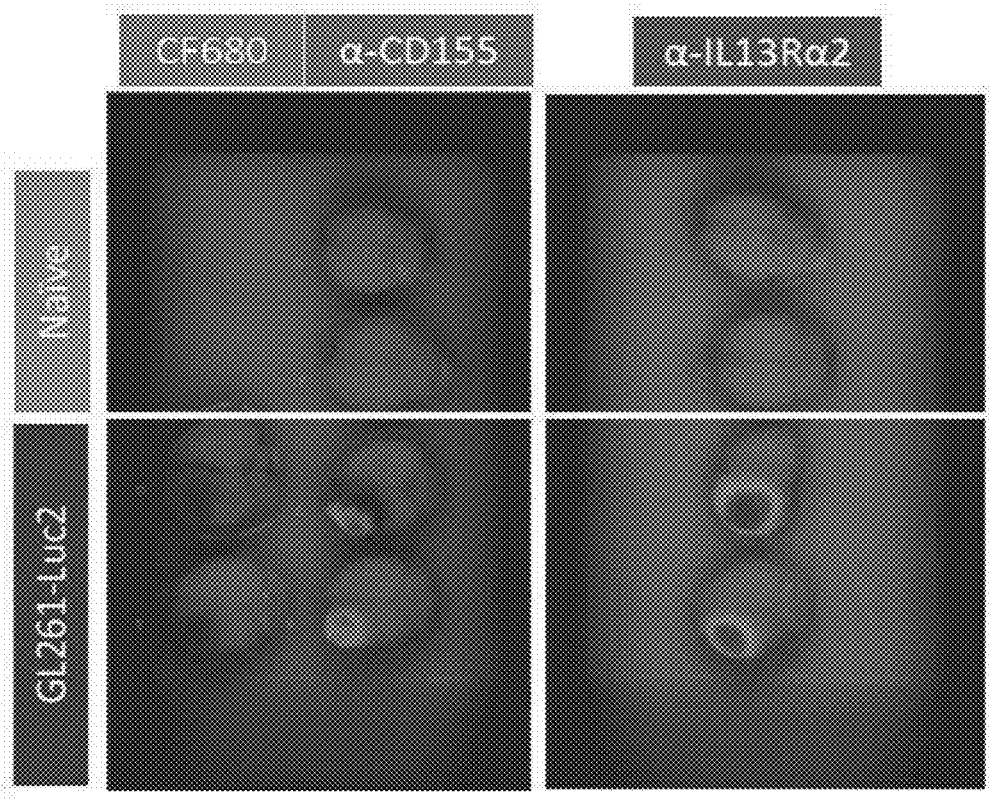
Figure 1. Anti-IL-13 alpha 2 Antibodies and Anti-CD155 Antibodies cross the BBB In Vivo.

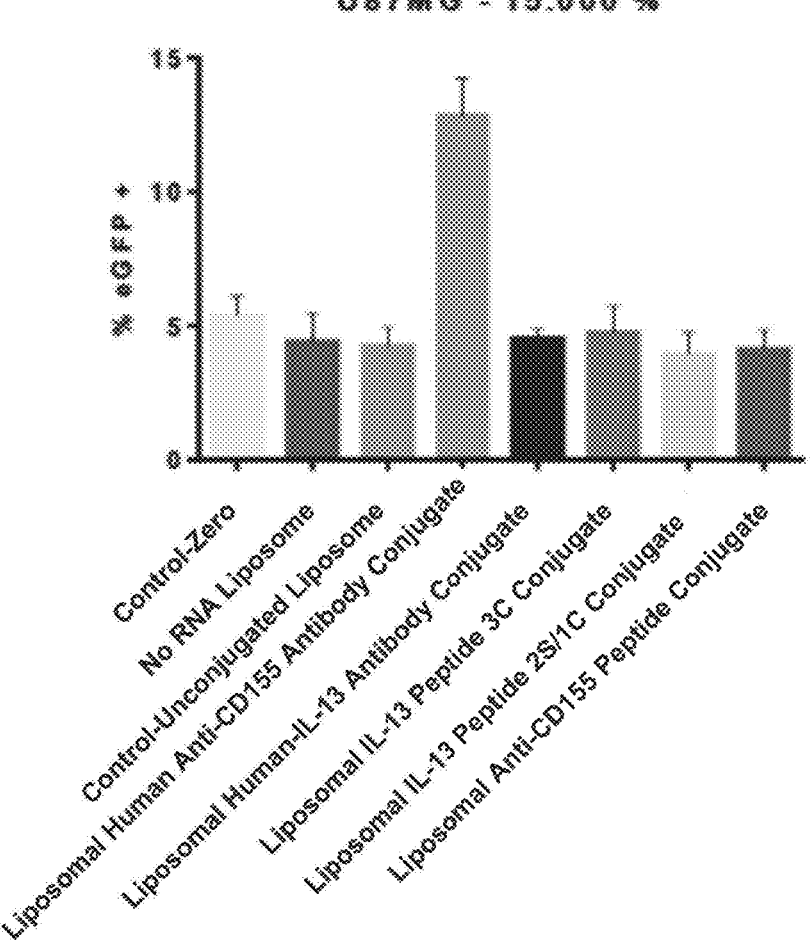
Figure 2. The D171 Monoclonal Antibody conjugated to mRNA is internalized and expressed in U87 tumors In Vitro.

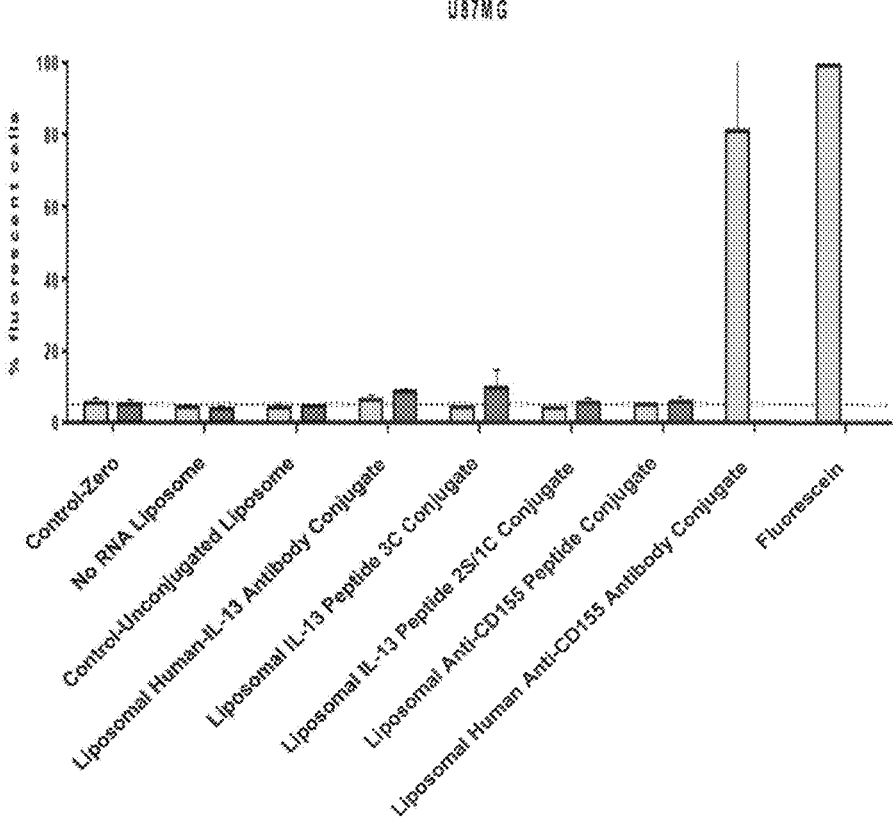
Figure 3. The D171 Antibody against human CD155 conjugated with fluorescein labeled mRNA is detected in U87 cells.

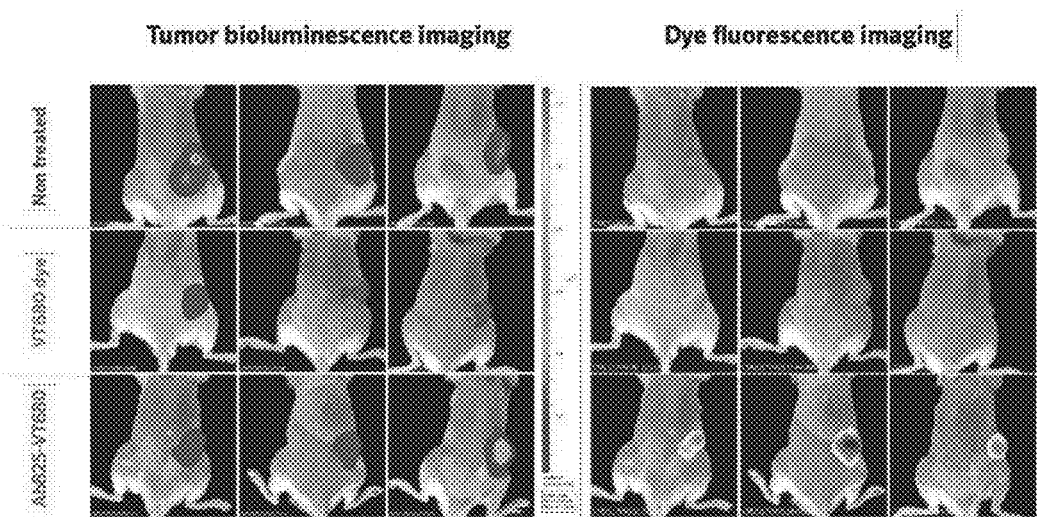
Figure 4. Comparison of tumor bioluminescence and dye fluorescence imaging 72 hours after injection of Ab825-VT680 and control VT680 in mice with U87MG tumor.

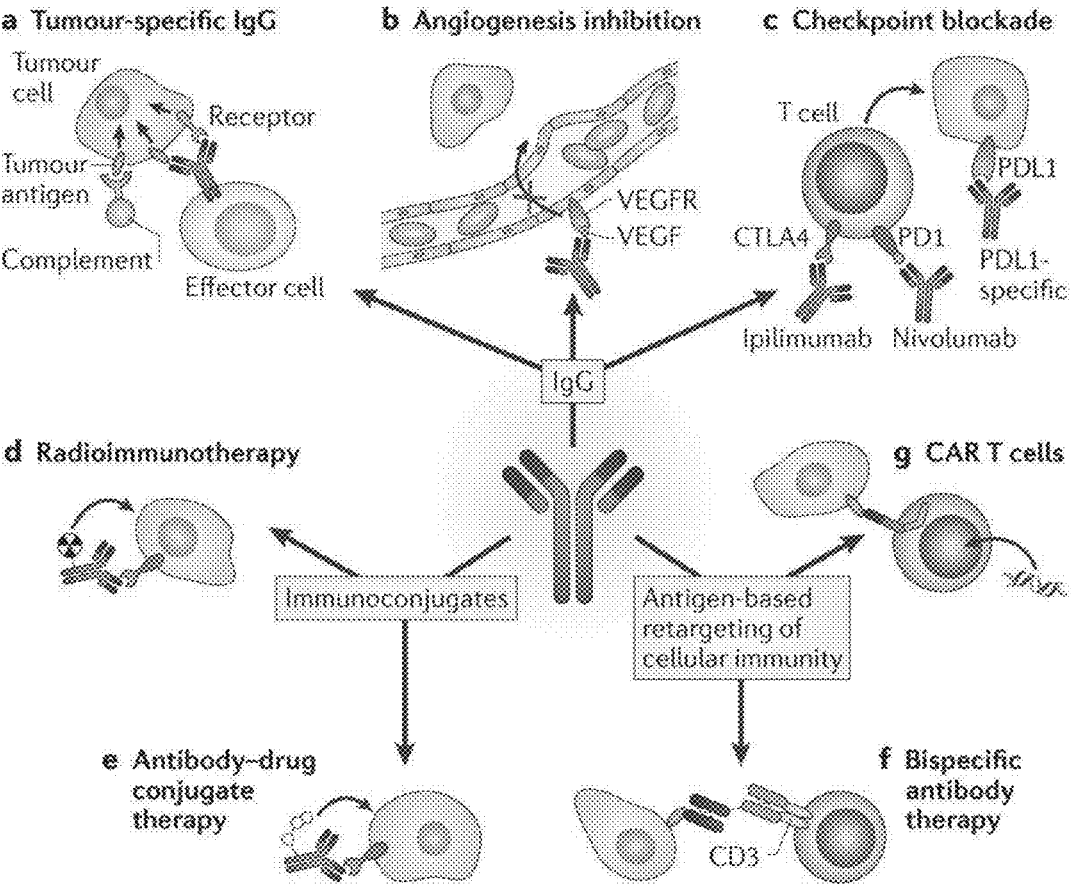
Figure 5. Mechanisms of Action for Therapeutic Antibodies and Antigen binding fragments.

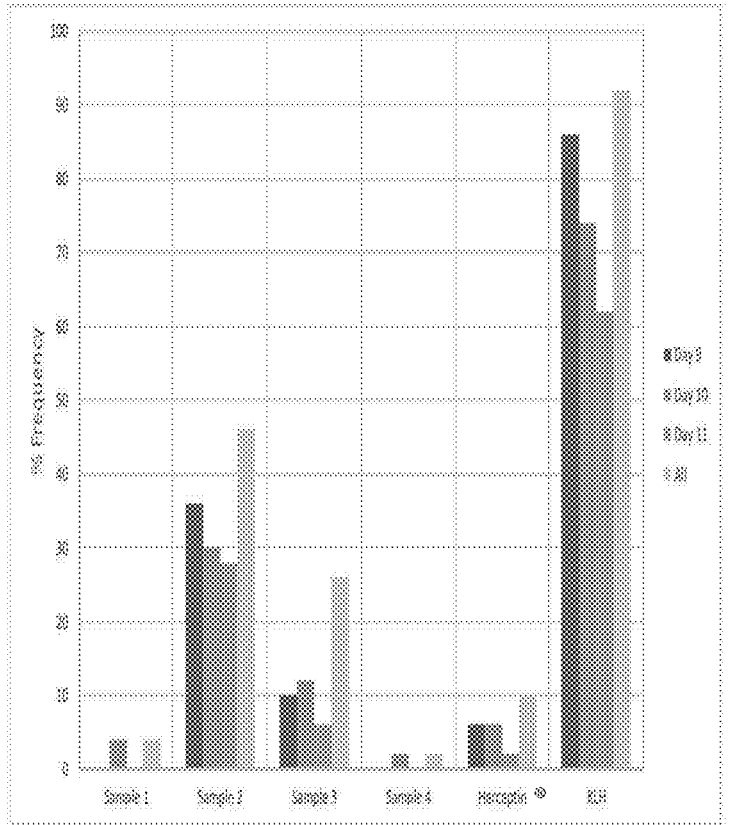
Figure 6. DC T Cell Assay of Anti-CD155 Humanized Monoclonal Antibodies.

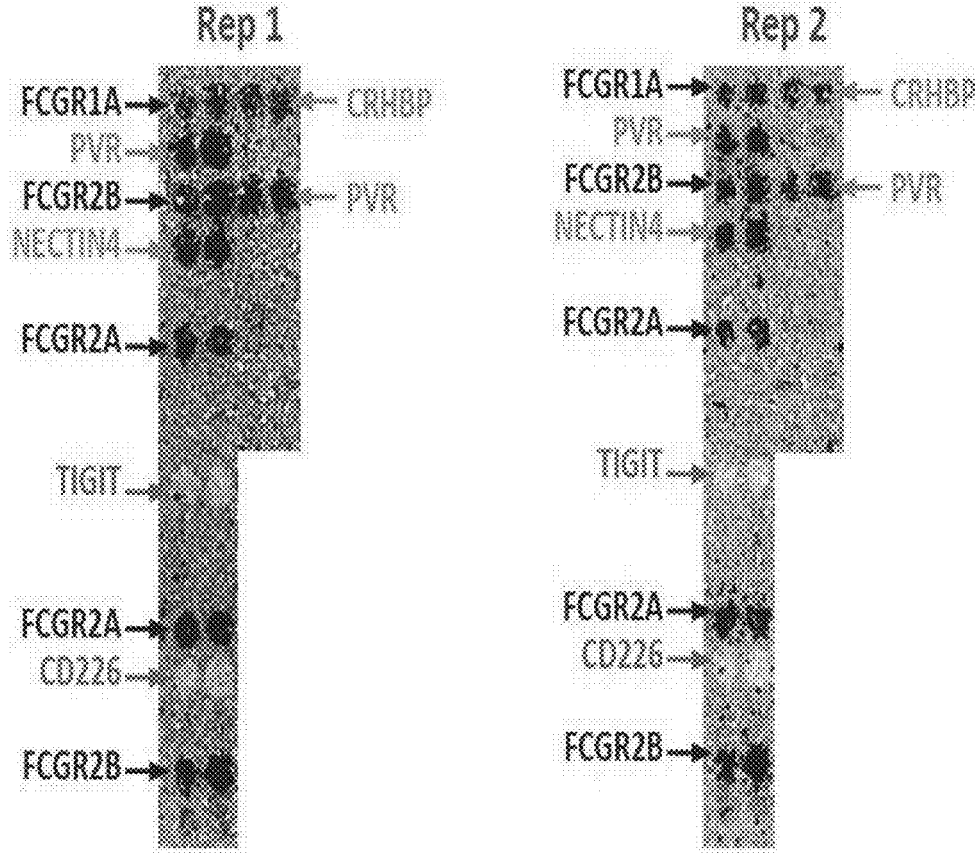
Figure 7. Binding Assay shows strong and specific binding of the Anti-CD155 humanized antibodies with cell membrane receptors PVR and Nectin 4. No Cell Fixation (FCGR1A is Fc Gamma Receptor 1A, FCGR2A is Fc Gamma Receptor 2A, FCGR2B is Fc Gamma Receptor 2B and CRHBP is Corticotropin Releasing Hormone Binding Protein).

| Antibody Variant | HAP-1 | | Vero | | U-87 | |
| --- | --- | --- | --- | --- | --- | --- |
| | EC$_{50}$ (µg/ml) | Relative EC$_{50}$[a] | EC$_{50}$ (µg/ml) | Relative EC$_{50}$[a] | EC$_{50}$ (µg/ml) | Relative EC$_{50}$[a] |
| VH3 / VK3 | 0.0474 | 1.00 | 0.0857 | 1.00 | 0.0869 | 1.00 |
| VH3 N54Q D56E / VK2 N92E | 0.1675 | 3.44 | 0.2258 | 2.63 | 0.2721 | 3.13 |
| VH3 N54E D56G / VK2 N92Q | 0.0372 | 0.79 | 0.0615 | 0.72 | 0.0689 | 0.79 |
| VH3 N54Q D56E / VK3 N92E | 0.1153 | 2.37 | 0.273 | 3.18 | 0.2839 | 3.27 |
| VH3 N54E D56G / VK3 N92Q | 0.0804 | 0.78 | 0.0563 | 0.65 | 0.0078 | 0.90 |
| VH4 N54Q D56E / VK3 N92E | 0.097 | 1.99 | 0.6295 | 7.32 | 0.5515 | 6.35 |
| VH4 N54E D56E / VK3 N92E | 0.0939 | 2.02 | 0.236 | 2.75 | 0.585 | 6.73 |
| VH4 N54E D56G / VK3 N92E | 0.0562 | 1.15 | 0.1078 | 1.25 | 0.1913 | 2.20 |
| VH4 N54Q D56E / VK3 N92Q | 0.1081 | 2.22 | 0.4803 | 5.59 | 0.5233 | 6.02 |
| VH4 N54E D56G / VK3 N92Q | 0.0459 | 0.91 | 0.0865 | 1.01 | 0.0933 | 1.07 |
| Irrelevant IgG1 | - | - | - | - | - | - |

Figure 8. Cell Binding Studies with EC 50 of Anti-CD155 Humanized Monoclonal Antibodies with HAP1 Cells, Vero Cells and U87 Cells.

SEQUENCE LISTING

```
<160> NUMBER OF SEQ ID NOS: 31

<210> SEQ ID NO 1
<211> LENGTH: 116
<212> TYPE: PRT
<213> ORGANISM: Artificial Sequence
<220> FEATURE:
<223> OTHER INFORMATION: synthesized sequence

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile His Pro Asn Asn Gly Asp Thr Ser Tyr Asn Gln Arg Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Thr Gly Asp Phe Asp Tyr Trp Gly Gln Gly Thr Thr Leu
            100                 105                 110

Thr Val Ser Thr
        115

<210> SEQ ID NO 2
<211> LENGTH: 5
<212> TYPE: PRT
<213> ORGANISM: Artificial Sequence
<220> FEATURE:
<223> OTHER INFORMATION: synthesized sequence

<400> SEQUENCE: 2

Glu Tyr Thr Met His
1               5

<210> SEQ ID NO 3
<211> LENGTH: 17
<212> TYPE: PRT
<213> ORGANISM: Artificial Sequence
<220> FEATURE:
<223> OTHER INFORMATION: synthesized sequence

<400> SEQUENCE: 3
```

-continued

```
Gly Ile His Pro Asn Asn Gly Asp Thr Ser Tyr Asn Gln Arg Phe Lys
1               5                  10                  15

Gly

<210> SEQ ID NO 4
<211> LENGTH: 7
<212> TYPE: PRT
<213> ORGANISM: Artificial Sequence
<220> FEATURE:
<223> OTHER INFORMATION: synthesized sequence

<400> SEQUENCE: 4

Trp Thr Gly Asp Phe Asp Tyr
1               5

<210> SEQ ID NO 5
<211> LENGTH: 107
<212> TYPE: PRT
<213> ORGANISM: Artificial Sequence
<220> FEATURE:
<223> OTHER INFORMATION: synthesized sequence

<400> SEQUENCE: 5

Asp Ile Val Met Thr Gln Ser Pro Lys Phe Met Ser Thr Ser Val Gly
1               5                  10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: synthesized sequence

<400> SEQUENCE: 6

Lys Ala Ser Gln Asn Val Gly Thr Asn Val Ala
1               5                  10

<210> SEQ ID NO 7
<211> LENGTH: 7
<212> TYPE: PRT
<213> ORGANISM: Artificial Sequence
<220> FEATURE:
<223> OTHER INFORMATION: synthesized sequence

<400> SEQUENCE: 7

Ser Ala Ser Tyr Arg Tyr Ser
1               5

<210> SEQ ID NO 8
<211> LENGTH: 9
<212> TYPE: PRT
```

<213> ORGANISM: Artificial Sequence
<220> FEATURE:
<223> OTHER INFORMATION: synthesized sequence

<400> SEQUENCE: 8

```
Gln Gln Tyr Asn Ser Tyr Pro Tyr Thr
1               5
```

<210> SEQ ID NO 9
<211> LENGTH: 116
<212> TYPE: PRT
<213> ORGANISM: Artificial Sequence
<220> FEATURE:
<223> OTHER INFORMATION: synthesized sequence

<400> SEQUENCE: 9

```
Glu Val Gln Leu Gln Gln Ser Gly Pro Glu Leu Lys Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Pro His Gly Lys Gly Leu Glu Trp Ile
        35                  40                  45

Gly Gly Ile His Pro Asn Asn Gly Asp Thr Ser Tyr Asn Gln Arg Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Thr Gly Asp Phe Asp Tyr Trp Gly Gln Gly Thr Thr Val
            100                 105                 110

Thr Val Ser Ser
        115
```

<210> SEQ ID NO 10
<211> LENGTH: 116
<212> TYPE: PRT
<213> ORGANISM: Artificial Sequence
<220> FEATURE:
<223> OTHER INFORMATION: synthesized sequence

<400> SEQUENCE: 10

```
Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Pro His Gly Lys Gly Leu Glu Trp Ile
        35                  40                  45

Gly Gly Ile His Pro Asn Asn Gly Asp Thr Ser Tyr Asn Gln Arg Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115
```

<210> SEQ ID NO 11

<211> LENGTH: 116
<212> TYPE: PRT
<213> ORGANISM: Artificial Sequence
<220> FEATURE:
<223> OTHER INFORMATION: synthesized sequence

<400> SEQUENCE: 11

```
Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Asn Gly Asp Thr Ser Tyr Asn Gln Arg Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115
```

<210> SEQ ID NO 12
<211> LENGTH: 116
<212> TYPE: PRT
<213> ORGANISM: Artificial Sequence
<220> FEATURE:
<223> OTHER INFORMATION: synthesized sequence

<400> SEQUENCE: 12

```
Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Asn Gly Asp Thr Ser Tyr Asn Gln Arg Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115
```

<210> SEQ ID NO 13
<211> LENGTH: 116
<212> TYPE: PRT
<213> ORGANISM: Artificial Sequence
<220> FEATURE:
<223> OTHER INFORMATION: synthesized sequence

<400> SEQUENCE: 13

```
Glu Val Gln Leu Val Gln Ser Gly Ser Glu Leu Lys Lys Pro Gly Ala
1               5                   10                  15
```

-continued

```
Ser Val Lys Val Ser Cys Lys Ala Ser Gly Tyr Thr Phe Thr Glu Tyr
        20              25              30

Thr Met His Trp Val Arg Gln Pro Pro Gly Lys Gly Leu Glu Trp Ile
        35              40              45

Gly Gly Ile His Pro Asn Asn Gly Asp Thr Ser Tyr Asn Gln Arg Phe
        50              55              60

Lys Gly Arg Val Thr Ile Thr Val Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Trp Thr Gly Asp Phe Asp Tyr Trp Gly Gln Gly Thr Leu Val
        100             105             110

Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: synthesized sequence

<400> SEQUENCE: 14

Asp Ile Val Met Thr Gln Ser Pro Ser Phe Met Ser Thr Ser Val Gly
1               5               10              15

Asp Arg Val Thr Ile Thr Cys Lys Ala Ser Gln Asn Val Gly Thr Asn
        20              25              30

Val Ala Trp Tyr Gln Gln Lys Pro Gly Gln Pro Pro Lys Ala Leu Ile
        35              40              45

Tyr Ser Ala Ser Tyr Arg Tyr Ser Gly Val Pro Asp Arg Phe Thr Gly
        50              55              60

Ser Gly Ser Gly Thr Asp Phe Thr Leu Thr Ile Ser Ser Leu Gln Ser
65              70              75              80

Glu Asp Leu Ala Glu Tyr Phe Cys Gln Gln Tyr Asn Ser Tyr Pro Tyr
                85              90              95

Thr Phe Gly Gln Gly Thr Lys Leu Glu Ile Lys
        100             105

<210> SEQ ID NO 15
<211> LENGTH: 107
<212> TYPE: PRT
<213> ORGANISM: Artificial Sequence
<220> FEATURE:
<223> OTHER INFORMATION: synthesized sequence

<400> SEQUENCE: 15

Asp Ile Val Met Thr Gln Ser Pro Ser Ala Met Ser Ala Ser Val Gly
1               5               10              15

Asp Arg Val Thr Ile Thr Cys Lys Ala Ser Gln Asn Val Gly Thr Asn
        20              25              30

Val Ala Trp Tyr Gln Gln Lys Pro Gly Gln Pro Pro Lys Ala Leu Ile
        35              40              45

Tyr Ser Ala Ser Tyr Arg Tyr Ser Gly Val Pro Asp Arg Phe Thr Gly
        50              55              60

Ser Gly Ser Gly Thr Asp Phe Thr Leu Thr Ile Ser Ser Leu Gln Ala
65              70              75              80

Glu Asp Leu Ala Glu Tyr Phe Cys Gln Gln Tyr Asn Ser Tyr Pro Tyr
                85              90              95
```

```
Thr Phe Gly Gln Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: synthesized sequence

<400> SEQUENCE: 16

Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: synthesized sequence

<400> SEQUENCE: 17

Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 18
<211> LENGTH: 116
<212> TYPE: PRT
<213> ORGANISM: Artificial Sequence
<220> FEATURE:
<223> OTHER INFORMATION: synthesized sequence

<400> SEQUENCE: 18

Glu Val Gln Leu Val Gln Ser Gly Ser Glu Leu Lys Lys Pro Gly Ala
1               5                   10                  15
```

```
Ser Val Lys Ile Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Gln Gly Glu Thr Ser Tyr Asn Gln Arg Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: synthesized sequence

<400> SEQUENCE: 19

Asp Ile Val Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Glu Ser Tyr Pro Tyr
                85                  90                  95

Thr Phe Gly Gln Gly Thr Lys Leu Glu Ile Lys
            100                 105

<210> SEQ ID NO 20
<211> LENGTH: 116
<212> TYPE: PRT
<213> ORGANISM: Artificial Sequence
<220> FEATURE:
<223> OTHER INFORMATION: synthesized sequence

<400> SEQUENCE: 20

Glu Val Gln Leu Val Gln Ser Gly Ser Glu Leu Lys Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Ser Gly Gly Thr Ser Tyr Asn Gln Arg Phe
    50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

Ala Arg Trp Thr Gly Asp Phe Asp Tyr Trp Gly Gln Gly Thr Leu Val
            100                 105                 110

Thr Val Ser Ser
        115

<210> SEQ ID NO 21
<211> LENGTH: 107
<212> TYPE: PRT
<213> ORGANISM: Artificial Sequence
<220> FEATURE:
<223> OTHER INFORMATION: synthesized sequence

<400> SEQUENCE: 21

Asp Ile Val Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Gln Ser Tyr Pro Tyr
                85                  90                  95

Thr Phe Gly Gln Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: synthesized sequence

<400> SEQUENCE: 22

Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Gln Pro Pro Lys Ala Leu Ile
        35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Glu Ser Tyr Pro Tyr
                85                  90                  95

Thr Phe Gly Gln Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: synthesized sequence

<400> SEQUENCE: 23

```
Asp Ile Gln Met Thr Gln Ser Pro Ser Ala Met Ser Ala Ser Val Gly
1               5                   10                  15

Asp Arg Val Thr Ile Thr Cys Lys Ala Ser Gln Asn Val Gly Thr Asn
                20                  25                  30

Val Ala Trp Tyr Gln Gln Lys Pro Gly Gln Pro Pro Lys Ala Leu Ile
            35                  40                  45

Tyr Ser Ala Ser Tyr Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Leu Ala Glu Tyr Phe Cys Gln Gln Tyr Gln Ser Tyr Pro Tyr
                85                  90                  95

Thr Phe Gly Gln Gly Thr Lys Leu Glu Ile Lys
            100                 105
```

```
<210> SEQ ID NO 24
<211> LENGTH: 116
<212> TYPE: PRT
<213> ORGANISM: Artificial Sequence
<220> FEATURE:
<223> OTHER INFORMATION: synthesized sequence

<400> SEQUENCE: 24
```

```
Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Gln Gly Glu Thr Ser Tyr Asn Gln Arg Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115
```

```
<210> SEQ ID NO 25
<211> LENGTH: 116
<212> TYPE: PRT
<213> ORGANISM: Artificial Sequence
<220> FEATURE:
<223> OTHER INFORMATION: synthesized sequence

<400> SEQUENCE: 25
```

```
Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
                20                  25                  30

Thr Met His Trp Val Arg Gln Pro His Gly Lys Gly Leu Glu Trp Ile
            35                  40                  45

Gly Gly Ile His Pro Asn Ser Gly Gly Thr Ser Tyr Asn Gln Arg Phe
        50                  55                  60

Lys Gly Arg Val Thr Ile Thr Val Asp Lys Ser Thr Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: synthesized sequence

<400> SEQUENCE: 26

Glu Val Gln Leu Val Gln Ser Gly Ser Glu Leu Lys Lys Pro Gly Ala
1               5                   10                  15

Ser Val Lys Val Ser Cys Lys Thr Ser Gly Tyr Thr Phe Thr Glu Tyr
            20                  25                  30

Thr Met His Trp Val Arg Gln Pro His Gly Lys Gly Leu Glu Trp Ile
        35                  40                  45

Gly Gly Ile His Pro Asn Ser Gly Glu Thr Ser Tyr Asn Gln Arg Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Thr Gly Asp Phe Asp Tyr Trp Gly Gln Gly Thr Leu Val
            100                 105                 110

Thr Val Ser Ser
        115

<210> SEQ ID NO 27
<211> LENGTH: 17
<212> TYPE: PRT
<213> ORGANISM: Artificial Sequence
<220> FEATURE:
<223> OTHER INFORMATION: synthesized sequence

<400> SEQUENCE: 27

Gly Ile His Pro Asn Gln Gly Glu Thr Ser Tyr Asn Gln Arg Phe Lys
1               5                   10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: synthesized sequence

<400> SEQUENCE: 28

Gln Gln Tyr Glu Ser Tyr Pro Tyr Thr
1               5

<210> SEQ ID NO 29
<211> LENGTH: 17
<212> TYPE: PRT
<213> ORGANISM: Artificial Sequence
<220> FEATURE:
<223> OTHER INFORMATION: synthesized sequence
```

-continued

```
<400> SEQUENCE: 29

Gly Ile His Pro Asn Ser Gly Gly Thr Ser Tyr Asn Gln Arg Phe Lys
1               5                   10                  15

Gly

<210> SEQ ID NO 30
<211> LENGTH: 9
<212> TYPE: PRT
<213> ORGANISM: Artificial Sequence
<220> FEATURE:
<223> OTHER INFORMATION: synthesized sequence

<400> SEQUENCE: 30

Gln Gln Tyr Gln Ser Tyr Pro Tyr Thr
1               5

<210> SEQ ID NO 31
<211> LENGTH: 17
<212> TYPE: PRT
<213> ORGANISM: Artificial Sequence
<220> FEATURE:
<223> OTHER INFORMATION: synthesized sequence

<400> SEQUENCE: 31

Gly Ile His Pro Asn Ser Gly Glu Thr Ser Tyr Asn Gln Arg Phe Lys
1               5                   10                  15

Gly
```

ANTIBODIES AND ANTIGEN BINDING FRAGMENTS AGAINST CD155 METHODS OF USE THEREOF

CROSS REFERENCE TO RELATED APPLICATIONS

This application is a continuation-in-part of application Ser. No. 16/365,330 filed on Mar. 26, 2019, which application is a continuation of application Ser. No. 16/247,278, filed Jan. 14, 2019, which application is a continuation-in-part of application Ser. No. 15/227,339, filed Aug. 3, 2016, which claims priority to U.S. Provisional Application Ser. No. 62/200,506, filed Aug. 3, 2015, all of which are incorporated by reference herein in their entirety.

REFERENCE TO A SEQUENCE LISTING

This application includes an electronic sequence listing in a file named CD155 Sequence Listing_ST25 created on Aug. 19, 2021 and containing 27 KB, which is hereby incorporated by reference.

FIELD

The disclosure relates generally to treatment of diseases utilizing monoclonal antibodies. This disclosure relates specifically to targeting cells expressing either the Poliovirus Receptor (PVR), also interchangeably referred to herein as CD155, or Nectin 4 (or both) with the anti-CD155 antibodies or antigen-binding fragments (antibody fragments) disclosed here. Antibodies against CD155 disclosed in this application bind the poliovirus receptor and additionally bind Nectin 4. CD155 and Nectin 4 are receptors that are overexpressed in numerous primary and metastatic tumors. CD155 and Nectin 4 have also been identified as ligands for the checkpoint molecule, T cell immunoglobulin and ITIM domain (TIGIT).

BACKGROUND

CD155 and family of receptors is found in various tissues in humans and other animals. In mice, the murine ortholog of CD155 is known as Tage 4. CD155 and Nectin 4 have been described as novel checkpoints. Whereas the CD155 receptor may have a role in normal development, this receptor is overexpressed in certain pathological conditions including malignancies such as glioblastoma multiforme (GBM), breast cancer including triple negative breast cancer (TNBC), leukemias (including AML), sarcomas, ovarian carcinoma, colon cancer, pancreatic cancer, lung cancer and rare but deadly cancers such as malignant peripheral nerve sheath tumor. CD155 plays a role in cell adhesion, motility, apoptosis, proliferation and metastasis. Modified poliovirus has been utilized as a vector to treat cancers overexpressing CD155 by direct local administration into tumor. Systemic administration of modified poliovirus therapeutics for cancer is not feasible as the majority of the population in the world is vaccinated against the poliovirus and poliovirus based therapeutics will likely be neutralized by the immune system upon systemic administration.

It would be advantageous to have an antibody based therapeutic against CD155 that can treat CNS cancers and systemic cancers. Such CD155 antibody can also enter the central nervous system either by crossing the blood brain barrier or thru other routes either as a therapeutic in and of itself or as a delivery agent for another therapeutic. In this disclosure, it is shown that a monoclonal antibody targeting mouse CD155 can enter the central nervous system upon systemic administration and can cross the blood brain barrier in mice with GL261 tumors in the brain in vivo. In an embodiment monoclonal antibodies targeting the human and mouse CD155 have also been shown to be internalizable and utilized to deliver and express payload, such as mRNA. There are known antibodies and peptides that cross the blood brain barrier in humans. For example, antibodies or antigen binding fragments against the transferrin receptor have been shown to cross the blood brain barrier in animal models and more recently in humans. Sequences for single domain antibodies or polypeptides such as FC5 and FC44 are also known in the art and FC5 and FC44 cross the blood brain barrier. Therapeutics incorporating blood brain barrier crossing molecules have entered or will enter clinical trials. Antibodies or ligands against the insulin receptor and insulin growth factor 1 receptor are yet other examples of peptides and proteins that cross the blood brain barrier and can be fused to the anti-CD155 antibodies described in this invention. In an embodiment, the anti-CD155 antibody is fused either chemically or through recombinant molecular biology with proteins or peptides to permit the anti-CD155 antibody to cross the blood brain barrier. Anti-CD155 antibodies, including D171, Ab825 and any humanized versions thereof, can be fused or chemically ligated or produced with recombinant technology to peptides or proteins (or antibodies) such as FC5, FC44, anti-type 1 insulin-like growth factor receptor (IGF1R) as well as anti-transferrin receptor antibodies (against transferrin receptor 1 or transferrin receptor 2) and antigen binding fragments. Such constructs will facilitate the crossing of the anti-CD155 antibodies across the blood brain barrier.

SUMMARY

CD155 and Nectin 4 have been described as novel checkpoints and the role of these novel checkpoints are of great import in immunooncology. Binding of CD155 to T cell immunoglobulin and ITIM domain (TIGIT) leads to inhibition of T cells and NK Cells. Recently, Nectin 4 has also been shown to bind TIGIT whereby tumors expressing Nectin 4 are thought to inhibit immune cells, particularly T cells. Furthermore, soluble CD155 levels are generally higher in patients with tumors that overexpress CD155. Elevated levels of membranous CD155 and soluble CD155 (sCD155) may have an immunosuppressive effect at least in part by downregulating DNAM 1 (CD226). Antibodies described in this invention against CD155 can bind CD155 (membranous or soluble CD155) leading to upregulation of DNAM 1 (CD226). Also, antibodies that bind to both CD155 and Nectin 4 can be used to target cancers that overexpress either CD155 or Nectin 4 (or cancers that express both CD155 and Nectin 4). Anti-CD155 antibodies can be used to block checkpoint pathways or they can be used to produce bispecific antibodies that bind to CD155 (or Nectin 4) and also bind T cells or NK cells thus engaging T cells or NK cells to kill the tumor cells. To date, no ADCs targeting CD155 are in clinical trials and none have been approved by the FDA. However, Enfortumab Vedontin, which targets Nectin 4, is an FDA approved ADC for the treatment of bladder cancer. Antibody drug conjugates can be prepared using the humanized antibodies described here to treat patients with cancers that overexpress CD155 (or Nectin 4). As part of this disclosure, antibodies against CD155 have been shown to deliver payload. In this case, mRNA was delivered and expressed in cancer cells overexpressing CD155. Furthermore, the antigen binding fragments that bind CD155 or Nectin 4 can be incorporated into Chimeric Antigen Receptors of immune cells (i.e. CART Cells and CAR NK Cells) for treatment of tumors expressing either Nectin 4 or CD155. Antibodies or antigen binding fragments against CD155 can also be used in combination with other small molecule therapeutics such as tyrosine kinase inhibitor and PARP inhibitors as well as combinations with antibodies against known checkpoint targets. The antibodies of this disclosure can be used in combination with one or more checkpoint inhibitors targeting CTLA 4, PD1, PDL1, CD112R, OX 40, TIGIT, NKG2A, CEACAM 1, B7H3, B7-H4, VISTA, LAG3, CD137, KIR, TIM 1, TIM3, LAIR 1, HVEM, BTLA, CD160, CD200, CD200R and A2r and other checkpoints are well known in the art. In an embodiment, the antibodies and antigen binding fragments against CD155 and Nectin 4 described here can also be developed as theranostics where the antibody or antigen binding fragments against CD155 comprises a radioactive label from one of the following (a) I-124 (b) Gallium 68 or (c) Lutetium 177 for either the diagnosis or the treatment of cancer.

This disclosure pertains to the treatment of various diseases with monoclonal antibodies against CD155 and Nectin 4. An embodiment of the disclosure is a method of treating a systemic or neurological disorder in a mammal comprising administering to a patient a composition comprising: a therapeutic agent; and a non-viral ligand capable of binding to CD155, wherein the ligand is conjugated to the therapeutic agent to treat a neurological disorder or systemic disorder. In an embodiment, the neurological disorder is a primary or metastatic brain tumor. In an embodiment, the neurological or systemic disorder is at least one from the group consisting of the following primary or metastic cancers (i) glioblastoma multiforme; (ii) neuroblastoma; (iii) oligodendroglioma, (iv) glioma, (v) astrocytoma, (vi) anaplastic astrocytoma, and (vii) meningioma, and (viii) primary or metastatic cancer of the breast, lung, kidney, pancreas and metastatic melanoma. In an embodiment, the disorder is at least one from the group consisting of (i) breast cancer (including TNBC); (ii) lung adenocarcinoma; (iii) melanoma; (iv) ovarian cancer; (v) AML; (vi) sarcoma; (vii) leukemia; (viii) bladder cancer; (ix) pancreatic carcinoma; (x) cervix carcinoma; (xi) colorectal carcinoma; (xii) epidermoid carcinoma; (xiii) hepatocellular carcinoma; (xiv) malignant gliomas; (xv) malignant peripheral nerve sheath tumor and melanoma; In an embodiment, the tumor overexpresses CD155. In an embodiment, the tumor overexpresses Nectin 4. In an embodiment, the tumor expresses both CD155 and Nectin 4.

In an embodiment, the ligand is at least one from the group consisting of: (i) an antibody against CD155 or Nectin 4; (ii) an antigen binding fragment against CD155 or Nectin 4. In an embodiment, the ligand is one which crosses the blood-brain barrier. In an embodiment, a fusion protein includes a first segment binding to CD155 and a second segment which is the therapeutic agent. In an embodiment, the antibody or antigen binding fragment is conjugated to the therapeutic agent where the therapeutic agent is at least one from the group consisting of (i) a drug; (ii) a prodrug; (iii) siRNA; (iv) antisense DNA or RNA; (v) messenger RNA; and (vi) guide RNA for CRISPR (vii) a plasmid; (vii) a single or double stranded oligonucleotide (RNA or DNA); (viii) a peptide; (ix) a protein; (x) a gene and (xi) a toxin. In an embodiment, the ligand is capable of binding to Nectin, Nectin 2 (CD112), Nectin 4, Nec1, PVRL1, Nec1-1, Nec1-4, poliovirus receptor related 1 protein, or poliovirus receptor related 2 protein. In an embodiment, the antibody or the antigen binding fragment drug conjugate further comprises a liposome or lipid nanoparticle (LNPs) which encapsulates the therapeutic. In an embodiment, the liposome is a pegylated liposome cross-linked to the ligand. In an embodiment, the ligand is a D171 antibody or an antibody with a heavy chain variable region sequence or light chain variable region sequence with more than 75% homology to the sequence of the D171 heavy chain variable region or the sequence of the D171 light chain variable region.

In an embodiment, the anti-CD155 antibody specifically binds to any intracellular, transmembrane or extracellular epitope of CD155. In an embodiment, D171 specifically binds to amino acids 35 to 50 of CD155. In an embodiment, the antibody or antigen binding fragment against CD155 binds to a tumor and elicits an immune response against the cancerous growth or tumor. In an embodiment, at least one antibody selected from the group consisting of a full antibody, antigen binding fragments, Fab, Fab2, Fc, and scFv, variable region of the light chain and/or heavy chain comprise a first component binding to CD155 and a second component binds to an effector cell in order to engage T cells or NK cells or other immune cells or to stimulate antibody-dependent cell-mediated cytotoxicity (ADCC) or complement dependent cytotoxicity (CDC). In an embodiment, the at least one is selected from monoclonal antibody, polyclonal antibody, humanized antibody, and chimeric antibody. In an embodiment, the effector cell is at least one from the group consisting of natural killer cells and lymphocytes including cytotoxic T cells. In an embodiment, the antibody is administered by at least one method from the group consisting of intravenously, intra-arterially, intratumorally, intrathecally, intramuscularly, subcutaneously, intravesicularly (i.e bladder), intraperitoneally, and via convection-enhanced delivery.

In an embodiment, at least one antibody selected from the group consisting of a full antibody, antigen binding fragments, Fab, Fab2, Fc, and scFv or other antigen binding fragments comprising a first component binding to CD155 and a second component binding to an effector cell in order to stimulate antibody-dependent cell-mediated cytotoxicity or complement dependent cytotoxicity (CDC). An embodiment of the disclosure is a method of delivering a therapeutic agent into the central nervous system either by systemic or local administration. In one embodiment, the anti-CD155 antibody or antigen binding fragments may cross the blood brain barrier of a mammal comprising administering into the bloodstream of the mammal a nonviral ligand targeting CD155 wherein the non-viral ligand is conjugated with a therapeutic agent. In an embodiment, the mammal has a brain tumor. In an embodiment, the mammal suffers from an adverse condition of the brain which is not a tumor. In one embodiment the anti-CD155 antibody or antigen binding fragments is itself a therapeutic or it delivers a therapeutic for the treatment of a systemic disorder such as cancer of the kidney, pancreas, ovaries, lungs, colon and sarcoma such as malignant peripheral nerve sheath tumor (MPNST).

In an embodiment, a nucleic acid-based drug is conjugated to an anti-CD155 antibody or antigen binding fragment. In an embodiment, a nucleic acid-based drug is conjugated to an anti-Nectin 4 antibody which also binds CD155. An embodiment of the disclosure is a composition comprising a humanized D171 antibody or a humanized Ab825. An embodiment of the disclosure is a humanized Anti-CD155 antibody such as the humanized Ab825 comprising a selenocysteine residue greater than 10 amino acids from the C-terminus.

An embodiment of the disclosure is a humanized D171 antibody or a humanized Ab825 antibody comprising an Fc region optimized to enhance ADCC. An embodiment of the disclosure is a humanized D171 antibody or a humanized Ab825 antibody optimized for CDC. An embodiment of the disclosure is a humanized D171 antibody or a humanized Ab825 antibody conjugated to a contrast agent for MRI/CT. An embodiment of the disclosure is a humanized D171 antibody or a humanized Ab825 antibody conjugated to diagnostic agents for a PET scan. An embodiment of the disclosure is a humanized D171 antibody or a humanized Ab825 antibody conjugated to a fluorescent probe such as IR800. An embodiment of the disclosure is a humanized D171 antibody or a humanized Ab825 antibody conjugated to a radiosensitizing drug. An embodiment of the disclosure is a humanized D171 antibody or a humanized Ab825 antibody conjugated to a chelator. In embodiment of the disclosure is a humanized D171 antibody or a humanized Ab825 antibody conjugated to a radioisotope. An embodiment of the disclosure is a humanized D171 antibody or a humanized A8b25 antibody conjugated to a nucleic acid therapeutic such as mRNA, siRNA, RNA or DNA oligonucleotide, a single or double stranded DNA. An embodiment of the disclosure is a humanized D171 antibody or a humanized Ab825 antibody, wherein the humanized D171 antibody or the humanized Ab825 antibody is the therapeutic. An embodiment of the disclosure is a humanized D171 antibody or a humanized Ab825 antibody wherein the humanized D171 antibody or the humanized Ab825 blocks the binding of the CD155 (poliovirus receptor) to TIGIT. An embodiment of the disclosure is a humanized D171 antibody or a humanized Ab825 antibody, wherein a humanized D171 antibody or a humanized Ab825 antibody blocks the binding of Nectin 4 to TIGIT An embodiment of the disclosure is a humanized D171 antibody or a humanized Ab825 antibody, wherein a humanized D171 antibody or a humanized Ab825 blocks CD155 (poliovirus receptor) thereafter upregulating the expression of DNAM 1 on NK cells or on T cells (or both). An embodiment of the disclosure is a humanized D171 antibody or a humanized Ab825 antibody, wherein the humanized D171 antibody or the humanized Ab825 blocks CD155 (poliovirus receptor) thereafter upregulating the expression of DNAM 1 on T cells. All of the above also apply to antigen binding fragments against CD155 and Nectin 4.

An embodiment of the disclosure is a method of identifying the extent of a tumor in a mammal overexpressing CD155 comprising the steps of administering a antibody or antigen binding fragment that binds CD155 where the antibody or antigen binding fragment has been conjugated with a label. In an embodiment, the label is at least one selected from the group consisting of a radioisotope, a chromophore, a fluorophore, and an enzyme. In an embodiment, the label is selected from the group consisting of a gamma ray or positron emitting radioisotope, a magnetic resonance imaging contrast agent, an X-ray contrast agent, and an ultrasound contrast agent. In an embodiment, a selenocysteine residue is utilized to conjugate the label with the antibody or antigen binding fragment against CD155. In an embodiment, the imaging is conducted through at least one technique selected from the group consisting of CT, ultrasound, MRI, SPECT and PET. In an embodiment, the imaging is performed during at least one time selected from the group consisting of pre-operative, intra-operative, and post-operative. An embodiment of the disclosure is a method of delivering a therapeutic agent across the blood brain barrier where the therapeutic agent is conjugated to an anti-CD155 antibody or antigen binding fragments. The foregoing has outlined rather broadly the features of the present disclosure in order that the detailed description that follows may be better understood. Additional features and advantages of the disclosure will be described hereinafter, which form the subject of the claims. In an embodiment, the primary or metastatic tumor overexpresses CD155. In an embodiment, the primary or metastatic tumor overexpresses Nectin 4.

In an embodiment, the anti-CD155 antibody or antigen binding fragment described in this disclosure is expressed as part of a therapeutic Chimeric Antigen Receptor T-cell (CART) or a therapeutic Chimeric Antigen Receptor NK cell for the treatment of CD155 positive tumors. In an embodiment, a humanized antibody or antigen binding fragment described in this disclosure is expressed as part of a therapeutic Chimeric Antigen Receptor T-cell (CART) or a therapeutic Chimeric Antigen Receptor NK cell for the treatment of Nectin 4 positive tumors.

In an embodiment, the anti-CD155 antibody or antigen binding fragment is capable of crossing the blood-brain barrier. In an embodiment, a fusion protein includes at least two segments where the first segment binds to CD155 or Nectin 4 and a second segment facilitates the crossing of the blood brain barrier. In an embodiment, the cell therapeutics comprise T cells expressing the antigen binding fragment which binds CD155 and/or Nectin 4. In an embodiment, the method further comprises a liposome or a polyethylenimine (PEI) polymer or a lipid nanoparticle (LNP). In an embodiment, a humanized D171 antibody or antibody with at least 90% homology to the D171 antibody specifically binds to amino acids 35 to 50 of CD155. In an embodiment, the anti-CD155 antibody or antigen binding fragment binds to the primary or metastatic tumor expressing CD155 and/or Nectin 4 and after binding elicits an immune response against the primary or metastatic tumor.

In an embodiment, at least one antibody or fragment selected from the group consisting of a full antibody, antigen binding fragments, Fab, Fab2, Fc, scFv comprise a first component binding to CD155 and a second component binding to an effector cell. In an embodiment, the at least one selected from the group consisting of a full antibody, antigen binding fragments, Fab, Fab2, Fc, scFv, is selected from monoclonal antibody, humanized antibody, chimeric antibody. In an embodiment, patients can be treated by injecting into a patient the antibody or an antigen binding fragments, or a DNA encoding the antibody (or antigen binding fragments) of any one of the above described antibodies, wherein the injection is at least one of intravenous, intra-arterial, intramuscular, intrathecal, intraventricular, intra tumoral, subcutaneous, or intralymphatic, intravesicular (i.e Bladder cancer or ventricular tumors of the CNS) and intratumoral and via convection-enhanced delivery.

An embodiment of the disclosure is a method of delivering a therapeutic agent across the blood brain barrier of a mammal comprising administering into the bloodstream of the mammal a non-viral ligand targeting CD155, wherein the non-viral ligand is conjugated with a therapeutic agent. In an embodiment, the non viral ligand is a monoclonal antibody or antigen binding fragment described in this application. In an embodiment, the therapeutic agent is encapsulated into a liposome and the liposome is conjugated to the monoclonal antibody or antigen binding fragment that binds CD155 and/or nectin 4. In an embodiment, the mammal has a brain tumor. In an embodiment, the mammal has an adverse condition of the brain, wherein the adverse condition of the brain is not a tumor. In an embodiment, the therapeutic agent is conjugated to an anti-CD155 antibody or antigen binding fragments. In an embodiment, the therapeutic agent is conjugated to an anti-CD155 antibody or anti-CD155 antigen binding fragments and is administered to a mammal for treatment of motor neurons in the brain, brainstem, spinal cord, or other CD155-expressing cells in the brain. An embodiment of the disclosure is a method for delivering antibodies to the brain of a mammal by fusing an antibody or antigen binding fragment of another therapeutic antibody to an anti-CD155 antibody or antigen binding fragments. In an embodiment, the therapeutic antibody or therapeutic antigen binding fragments is fused to an anti-CD155 antibody or antigen binding fragment by a manner selected from the group consisting of chemically, antibody engineered, or avidin-biotin based crosslinking.

In an embodiment, the anti-CD155 antibody or antigen binding fragments that bind CD155 is the therapeutic in and of itself. In an embodiment, the anti-Nectin 4 antibody or antigen binding fragments is the therapeutic in and of itself. An embodiment of the disclosure is a method of identifying the extent of a tumor in a mammal overexpressing CD155 comprising the steps of administering a non-viral ligand targeting CD155 which has been conjugated with a label; and imaging the brain tumor. In an embodiment, the label is at least one selected from the group consisting of a radioisotope, a chromophore, a fluorophore, and an enzyme. In an embodiment, the label is selected from the group consisting of a gamma ray or positron emitting radioisotope, a magnetic resonance imaging contrast agent, an X-ray contrast agent, and an ultrasound contrast agent. In an embodiment, a selenocysteine residue within the antibody or antigen binding fragment is utilized to conjugate the label with the non-viral ligand. In an embodiment, the imaging is conducted through at least one technique selected from the group consisting of CT, ultrasound, MRI, SPECT and PET. In an embodiment, the imaging is performed during at least one time selected from the group consisting of pre-operative, intra-operative, and post-operative.

In an embodiment, a human or humanized antibody against the human poliovirus receptor is modified with a selenocysteine residue as one embodiment to facilitate stoichiometric conjugation to a reporter molecule for diagnosis of a disease or as a therapeutic for treatment. In an embodiment, a human or humanized antibody against the human poliovirus receptor is conjugated to a therapeutic such as small drug molecules either directly coupled or encapsulated in an nanoparticle being delivered to target cells overexpressing CD155 such as tumor cells. In an embodiment, a human or humanized antibody against the human poliovirus receptor is conjugated to a fluorophore or other reporter molecule for the non-operative, preoperative, intraoperative or postoperative diagnosis or treatment of target cells overexpressing the CD155 receptor such as tumor cells.

In an embodiment, a human or humanized antibody against the human poliovirus receptor is fused with a therapeutic peptide either thru antibody engineering or chemical coupling. In an embodiment, a human or humanized antibody against the human poliovirus receptor is fused with another therapeutic antibody (or antigen binding fragment) either chemically or thru antibody engineering in order to create bi-specific antibodies where one component is the human or humanized antibody (or antigen binding fragment) against the human poliovirus receptor. In an embodiment, a human or humanized antibody against the human poliovirus receptor binds tumor cells overexpressing CD155.

In an embodiment, a human or humanized antibody against the human poliovirus receptor also binds tumor cells over expressing Nectin 4. An embodiment of the disclosure is a humanized D171 antibody or humanized Ab825 or an antibody with a similar sequence to the D171 antibody comprising at least one selected from the group consisting of a selenocysteine residue greater than 10 amino acids from the C-terminus; an Fc region optimized to enhance ADCC; optimization for CDC; coupling to a contrast agent for MRI/CT; coupling to diagnostic agents for a PET scan; coupling to a fluorescent probe; coupling to a radiosensitizer; coupling to a chelator; coupling to radioisotopes; coupling to a therapeutic agent; and wherein a humanized anti-CD155 antibody is a therapeutic. An embodiment of the disclosure includes the humanized anti-CD155 antibodies or antigen binding fragments disclosed here bind the poliovirus receptor and inhibit the poliovirus receptor from binding to TIGIT. Another embodiment includes the humanized anti-CD155 antibody and antigen binding fragments disclosed here will bind Nectin 4 and inhibit Nectin 4 from binding to TIGIT.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope.

FIG. 1 shows that mouse Anti-IL-13 alpha 2 Antibodies and mouse Anti-CD155 Antibodies cross the BBB and bind mouse IL-13 alpha 2 (mIL-13 alpha 2) and mouse CD155 (mCD155) in GL261 tumors In Vivo. Fluorophore labeled Mouse anti-IL-13 alpha 2 receptor antibodies and Fluorophore labeled anti-CD155 antibodies, were injected into test mice. The fluorophore labeled antibodies crossed the blood brain barrier and accumulated in GL261 tumors in C57B16 mice. GL261 tumors express both receptors, the mouse CD155 and the mouse IL-13_alpha 2 receptor.

FIG. 2 shows that the D171 Monoclonal Antibody conjugated to liposome encapsulated eGFP mRNA is internalized and GFP is expressed in U87 tumors In Vitro. U87 Tumors overexpress Human CD155. D171 Monoclonal Antibody against human CD155 was conjugated with liposomal encapsulated eGFP mRNA and eGFP fluorescence in U87 cells was recorded after a 24 H exposure to 10 ng/well of eGFP encoding RNA containing liposomes functionalized with D171 antibody. Three Cellular Densities were explored FIG. 3 shows that the D171 Antibody against human CD155 conjugated with liposomal encapsulated fluorescein labeled mRNA and fluorescein was detected in approximately 80% of U87 cells. The D171 conjugate is internalized in U87 cells in vitro. U87 cells are known to overexpress CD155.

FIG. 4 shows a comparison of tumor bioluminescence and dye fluorescence imaging 72 hours after injection of Ab825-VT680 and control VT680 in mice with U87MG tumor. Ab825-VT680 conjugate binds and accumulates in U87MG tumors In Vivo. The control mice were either untreated or treated with VT 680 dye alone. The mice treated with the fluorophore labeled anti-CD155 antibody showed accumulation in the tumor as demonstrated with fluorescence imaging. Bioluminescence showed that the area of fluorescence accumulation correlated with the area of tumor seen with bioluminescence imaging.

FIG. 5 shows the potential mechanisms of action for anti-CD155 Antibodies and Antigen Binding Fragments. CD155-TIGIT interactions and CD155-CD96 interactions (not shown) is a target for Checkpoint blockade. The Anti-CD155 Antibody and Antigen Binding Fragments can be used for (a) ADCC (c) Checkpoint blockade, (d) Radioimmunotherapy, (e) Antibody Drug Conjugates (ADCs) (f) Bispecific Antibodies where one binds CD155 and the other binds a second receptor such as CD3 on T Cells and (g) to prepare anti-CD155 CART or CAR NK Cells. The Anti-CD155 Antibodies and Antigen Binding Fragments also bind Nectin 4 and the constructs described here can also target Nectin 4.

FIG. 6 shows the DC T Cell Assay in 50 patient samples with the Humanized Monoclonal Antibodies VH3 N54S D56G/Vk2 N92Q (Sample 2) and VH3 N54S D56G/Vk3N92Q (Sample 3) and VH4 N54S D56G/Vk3N92Q (Sample 4). The frequency of proliferation (% of patient samples with proliferation) and Stimulation Index (SI) for each of the tested antibodies and controls are shown.

FIG. 7 shows the binding assay results demonstrating strong and specific binding of the humanized antibodies against CD155 with cell membrane receptors PVR and Nectin 4. No Cell Fixation. Inverse Hit is seen with CD226 (DNAM 1) and TIGIT which are natural ligands of CD155. The assay was done with over 5000 membrane receptors. Strong and specific binding was seen with CD155 and Nectin 4. Inverse Hit (white spots) was seen with TIGIT and CD226 as these receptors are ligands for CD155 and bound to endogenous CD155 in the assay creating inverse hit spots.

FIG. 8. Cell Binding Studies with EC 50 for the Humanized Monoclonal Antibodies against CD155 with HAP1 Cells, Vero Cells and U87 Cells. The variants with N54S D56G in the heavy chain variable region (HCVR) and the variants with N92Q in the light chain variable region (LCVR) had higher affinity binding with CD155 when compared to the variants with N54Q D56E or N54S D56E in the HCVR or N92E in the LCVR.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

As used herein, "conjugated" refers to any manner in which the ligand is coupled to the therapeutic agent including, but not limited to, chemically, electrostatically or through the creation of fusion constructs of a ligand and therapeutic agent by employing all tools of molecular biology. The statement "all tools of molecular biology" includes but is not limited to production of custom Chimeric Antigen Receptors where an antibody or antigen binding fragments is incorporated into a Chimeric Antigen Receptor in CAR T cell therapy for eliminating disease, including but not limited to, cancer.

An antibody (Ab), also known as an immunoglobulin (Ig), is a large Y-shape protein produced by plasma cells that is used by the immune system to identify and neutralize foreign objects such as bacteria and viruses. The antibody recognizes a unique part of the foreign target, called an antigen. Each tip of the "Y" of an antibody contains a paratope (a structure analogous to a lock) that is specific for one particular epitope (similarly analogous to a key) on an antigen, allowing these two structures to bind together with precision.

A bispecific monoclonal antibody (BsMAb, BsAb) is an artificial protein that is composed of fragments of two different monoclonal antibodies and consequently binds to two different types of antigen. The most widely used application of this approach is in cancer immunotherapy, where BsMAbs are engineered so that it simultaneously binds to a cytotoxic cell (such as a receptor like CD3 on T cells) and a receptor on a tumor cell resulting in killing of the tumor cell.

The blood-brain barrier (BBB) is a highly selective permeability barrier that separates the circulating blood from the brain extracellular fluid (BECF) in the central nervous system (CNS). The blood-brain barrier is formed by capillary endothelial cells, which are connected by tight junctions with an extremely high electrical resistivity of at least $0.1\Omega\square$m. The blood-brain barrier allows the passage of water, some gases, and lipid soluble molecules by passive diffusion, as well as the selective transport of molecules such as glucose and amino acids that are crucial to neural function.

Conjugated includes but is not limited to molecular, chemical, and electrostatic binding. An example of molecular binding is antibody engineering. An example of a chemical bond is a covalent bond. An example of electrostatic binding is biotin and streptavidin.

CD155 is a Type I transmembrane glycoprotein in the immunoglobulin superfamily. Commonly known as Poliovirus Receptor (PVR) due to its involvement in the cellular poliovirus infection in primates, CD155's normal cellular function is in the establishment of intercellular adherens junctions between epithelial cells. CD155 is a transmembrane protein with 3 extracellular immunoglobulin-like domains, D1-D3, where D1 is recognized by the virus. Synonyms include PVR; CD155; HVED; NECL5; Necl-5; PVS; and TAGE4.

Fusion proteins or chimeric proteins are proteins created through the joining of two or more genes that originally coded for separate proteins. Translation of this fusion gene results in a single or multiple polypeptides with functional properties derived from each of the original proteins.

The fusion proteins are produced through molecular biology techniques or chemical coupling of two antibodies or antigen binding fragments.

In an embodiment, the antibody has functional groups available for modification with a label, crosslinker, or covalent modification. In an embodiment, the functional group on the antibody are primary amines, sulfhydryl groups, carbohydrates, selenocysteine, or incorporation of an unnatural amino acid.

In an embodiment, a crosslinker can be used to link a gene, polypeptide, or small molecule to an antibody. In an embodiment, the crosslinker can be a heterobifunctional crosslinker. In an embodiment, the heterobifunctional cross-linker is succinimidyl acetylthioacetate (SATA), succinim-idyl trans-4-(maleimidylmethyl)cyclohexane-1-carboxylate (SMCC), succinimidyl 3-(2-pyridyldithio) propionate (SPDP), 1-ethyl-3-(3-dimethylaminopropyl)carbodiimide (EDAC), N-((2-pyridyldithio)ethyl)-4-azidosalicylamide (PEAS; AET), 4-azido-2,3,5,6-tetrafluorobenzoic acid, suc-cinimidyl ester (ATFB, SE), benzophenone-4-maleimide, benzophenone-4-isothiocyanate, 4-benzoylbenzoic acid, succinimidyl ester, iodoacetamide azide, iodoacetamide alkyne, Click-iT maleimide DIBO alkyne, azido (PEO) 4 propionic acid, succinimidyl ester, alkyne, succinimidyl ester, or Click-iT succinimidyl ester DIBO alkyne. In another embodiment, the crosslinket can be a peptide cross-linker sensitive cathepsin cleavage. In another embodiment the crosslinker can be one used for site-specific crosslinking such as azide crosslinker with BCN for click chemistry. Available likers can be used to crosslink the antibody to the payload based on click chemistry using azides (N3). The reactive functional groups are the same on each end. The reactive ends often target primary amines and sulfhydryl groups. In an embodiment, azides react with alkynes via the copper-catalyzed azide-alkyne cycloaddition reaction. In another embodiment, a metal free azide-alkyne reaction can be used for conjugation. In an embodiment, the crosslinker reacts nonspecifically with available sites upon UV illumi-nation.

Human Antibodies are antibodies produced in human system or other mammalian systems or using yeast or phage technology. Humanized antibodies are antibodies from non-human species whose protein sequences have been modified to increase their similarity to antibody variants produced naturally in humans. The process of "humanization" is usually applied to monoclonal antibodies developed for administration to humans (for example, antibodies devel-oped as anti-cancer drugs). Humanization can be necessary when the process of developing a specific antibody involves generation in a non-human immune system (such as that in mice). The protein sequences of antibodies produced in this way are partially distinct from homologous antibodies occurring naturally in humans, and are therefore potentially immunogenic when administered to human patients.

Humanizing antibodies involves removing potentially immunogenic sequences in a non-human antibody. A less immunogenic sequence for humans may be inserted in place of the immunogenic sequence. There are many ways to humanize a particular antibody. In an embodiment, it may take over a year to humanize a particular non-human anti-body. In an embodiment, the non-human antibody is human-ized by 1) reviewing the structure to determine what sequences will be immunogenic to a human, 2) removing the sequences that will be immunogenic to a human, 3) main-taining or improving the ability of the antibody to bind to its target receptor, 4) assess the binding of the antibody to the target receptor, 5) screen for bad immunogenic responses, 6) remove the sequences responsible for the bad immunogenic response. In an embodiment, software is used to identify potentially immunogenic sequences to be removed. In an embodiment, there are still bad immunogenic responses after removing the sequences identified in the software and the software is not accurate. In an embodiment, in vitro studies are performed to determine which sequences to remove. When different parties humanize a given antibody, the sequence of the given antibody will likely be different. Mutations in the CDRs may be necessary in order to remove potential a separate isomerization sites and sites vulnerable to deamidation. Mutations in CDRs can affect binding and as such the antibody humanization is often limited to the framework residues. The goal of humanization and muta-tions of labile sites is to achieve a low risk of infusion reaction and a low risk of immunogenicity and to stabilize potential deamidation and isomerization sites within the CDRs. Even after humanization, different humanized anti-bodies may have different dissociation constants (Kd), dif-ferent profile on cytokine release assay, different immuno-genicity profiles based on Episcreen and DC TCell Episcreen assays. Humanization of antibody D171 or Ab825 has not been previously taught and is taught for the first time in this invention. Ab825 was found to have highest risk of infusion reaction when compared to the humanized variants.

In an embodiment, the anti-CD155 antibodies may be fused to another therapeutic antibody to navigate the thera-peutic antibody across the blood brain barrier. In an embodi-ment, the approved therapeutic antibody is not able to get across the blood brain barrier alone. In an embodiment, the anti-CD155 antibody travels retrograde through nerves and enters the CNS. In an embodiment, the anti-CD155 antibody travels through the blood-CSF barrier.

A ligand is a substance (usually a small molecule) that forms a complex with a biomolecule to serve a biological purpose. In protein-ligand binding, the ligand is usually a signal-triggering molecule, binding to a site on a target protein. In many examples described herein, the target protein to which the ligand binds is a receptor on a cell. An antibody or antigen binding fragment that binds CD155 is considered a ligand for CD155.

Non-viral means any polypeptide, including DNA/RNA segments and proteins, which lack sufficient structure to be considered a virus. Non-viral further excludes any complex polypeptide that is created through a process which begins with a virus and cleaves portions of the virus to create the polypeptide.

A polypeptide is linear chain of amino acid residues is called a polypeptide. A protein contains at least one long polypeptide. Short polypeptides, containing less than about 20-30 residues, are rarely considered to be proteins and are commonly called peptides, or sometimes oligopeptides.

The individual amino acid residues are bonded together by peptide bonds and adjacent amino acid residues.

A protein is a large biological molecule, or macromol-ecule, consisting of one or more long chains of amino acid residues. Proteins differ from one another primarily in their sequence of amino acids, which is dictated by the nucleotide sequence of their genes, and which usually results in folding of the protein into a specific three-dimensional structure that determines its activity.

A receptor is a protein molecule usually found embedded within the plasma membrane surface of a cell that receives chemical signals from outside the cell. When such chemical signals bind to a receptor, they cause some form of cellular/tissue response, e.g. a change in the electrical activity of the cell. In this sense, a receptor is a protein molecule that recognizes and responds to endogenous chemical signals. CD155 is also known as the poliovirus receptor.

"Therapeutically effective amounts" are amounts which eliminate or reduce the patient's tumor burden, or which prevent, delay or inhibit metastasis. The dosage will depend on many parameters, including the nature of the tumor, patient history, patient condition, the possible co-use of cytotoxic agents, and methods of administration. Methods of administration include injection (e.g. parenteral, subcutaneous, intravenous, intraperitoneal, intrathecal, convection enhanced etc.), for which the molecule or complex binding the PVR is provided in a nontoxic pharmaceutically acceptable carrier.

The delivery of an mRNA or gene for a reporter molecule EGFP (as an example) was delivered to cells expressing CD155 via a anti-CD155 Antibody conjugated to liposomes encapsulating nucleic acids, both in mice (against the mouse CD155) and human (against the human CD155) cell lines using monoclonal antibodies against the respective poliovirus receptor in these cell lines. D171 antibody was used to deliver liposome encapsulated mRNA to U87 tumors that express CD155. mRNA for GFP was expressed upon delivering mRNA conjugates of D171. This delivery system is extendable to other nucleic acids and drugs based on the results. The anti-CD155 monoclonal antibody unexpectedly enters the central nervous system and coated the tumor. The potential applications of this finding include the utilization of CD155 to facilitate transcytosis of ligands and ligand conjugates across the blood brain barrier or other barrier preventing entry into the CNS, providing a potential alternative to the transferrin receptor. Fusion of therapeutic peptides or proteins to antibodies against CD155 or antigen binding fragments against CD155 may provide a pathway to cross the blood brain barrier or other barrier preventing entry into the CNS. Antibodies against CD155 bind CD155 in human and mouse cell lines and are internalized by the mouse and human cells in vitro. An antibody against the mouse CD155 binds to tumor in vivo and crosses the blood brain barrier. Anti-CD155 antibodies have diagnostic potential in vivo for diagnosing CD155 tumors and for demarcation of CD155 tumors preoperatively, intraoperatively and postoperatively. The anti-CD155 antibodies may have therapeutic potential, either alone with induction of the immune system such as antibody directed cell cytotoxicity, or as Anti-CD155 antibodies fused to other peptides, polypeptides or antibodies. Various cargo such as toxins, proteins, peptides, small drug molecules, RNA or DNA based drugs such as genes, messenger RNA, and oligonucleotides. Each of the above can be directly coupled to the anti-CD155 antibody or the antibody against CD155 can be coupled to nanoparticles/ liposomes encapsulating toxins, proteins, peptides, small drug molecules, RNA or DNA based drugs such as genes, messenger RNA, oligonucleotides. The ligand-PVR interaction such as the anti-CD155 antibody-PVR may serve as transcytosis pathway for macromolecules across the blood brain barrier and may prove to be an alternative to transferrin. The Anti-CD155 antibody or any ligand binding the PVR, which crosses the blood brain barrier, can also serve as transporter of drugs, proteins, peptides, polypeptides that are fused or conjugated to the anti-CD155 antibody or other PVR ligand.

Ligands that can be used in the present disclosure include but are not limited to Anti-CD155 AB, Further included are Fusion Proteins of Antibodies and antigen binding fragments that bind CD155 (and/or Nectin 4) and fusion proteins of such antibodies and antigen binding fragments.

Still further included are Ligand Conjugates of Liposomes and Encapsulation of RNA or DNA or modified nucleic acids or other therapeutics and Ligand Conjugates of nucleic acids or other therapeutics without liposomes.

In an embodiment, the antibodies against CD155, capable of crossing the blood brain barrier are selected from the group include but are not limited to antigen binding fragments (Fab, FcV), humanized anti-CD155 antibodies, anti-CD155 antibodies targeting coupled liposome/nanoparticle and encapsulated or unencapsulated therapeutics including toxins, genes, DNA or RNA based drugs or other therapeutics; anti-CD155 antibody coupled to a fluorescent probe, or contrast agent for diagnosis of tumor or for the identification of tumor or tumor margins to assist in delineating tumor nonoperatively, preoperatively, intraoperatively or postoperatively; anti-CD155 antibody can be fused to proteins peptides toxins or other antibody or antigen binding fragments to be delivered across the blood brain barrier utilizing CD155 for transcytosis that upon crossing, either CD155 or the fused protein or both can then bind the target cell within the CNS; unconjugated Antibody against CD155 can serve as a therapeutic if it induces Antibody Directed Cell Cytotoxicity or Complement Directed Cytotoxicity in the CNS as well as non-CNS tumors with high CD155 expression.

Anti-CD155 antibody in mice unexpectedly crossed the blood brain barrier and bound to the tumor. Antibodies do not normally cross the BBB. Poliovirus itself has other pathways for entering the CNS. In an embodiment, the antibodies are used for treatment of neurological diseases. In an embodiment, it may be beneficial to deliver a substance across the blood brain barrier when there is not a tumor. In an embodiment the neurological disease is not a brain tumor. Antibodies are comprised of various portions including but not limited to the heavy chain, light chain, Fab, Fc, scFv, carbohydrate, variable region, and constant region.

The antibodies can be modified in ways including but not limited to glycomodification, alterations of the amino acids in the constant region, use of different human mAb isotype (e.g. IgG4), linking an isotope to mAb with a stable linker, linking a drug to the mAb with a cleavable linker, inserting DNA for mAb variable region fused to signaling peptide into T cell to induce expression of CAR, and crosslink regions from two mAbs.

Monoclonal Antibody based (mAb-based) therapeutics have many functions, including but not limited to antitumor mAbs, angiogenesis inhibition, T cell checkpoint blockade, radioimmunotherapy, antibody-drug conjugate, bispecific antibody, and chimeric antigen receptor T cell. One embodiment of this invention includes a bispecific antibody where one antibody or antigen binding fragment binds to CD155 (or Nectin 4) expressed on the tumor cell and the antibody or antigen binding fragment binds to CD3 (a T cell receptor) on T-cells thus approximating the T-cells to the tumor cells to enhance T cell mediated killing of tumor. Another embodiment includes a bispecific antibody where one antibody or antigen binsing fragment binds to CD155 (or Nectin 4) on the tumor cell and another antibody or antigen binding fragment binds a receptor on NK cells (i.e such as the CD16, NKG2D, SLAM receptor or natural cytotoxicity receptors such as NKp46, NKp44 or NKp30 on NK cells) thus approximating the NK cell to the tumor cells to enhance NK cell mediated killing of tumor. Immune mediated effects of tumor-specific IgG include, but are not limited to, ADCC, opsonization, and CDC. Direct effects of tumor-specific IgG are to block ligands, inhibit receptor dimerization, and induce apoptotic signaling. Bispecifics incorporating anti-CD155 antibodies and antigen binding fragments along with an antibody or antigen binding fragment that binds Type 1 Insulin like Growth Factor Receptor or FC 5 or FC 44 or transferrin receptor (Tfr1 or Tfr2) can be prepared to facilitate the crossing of the blood brain barrier.

A potential limitation to developing monoclonal antibodies for neurooncology is the inability to cross the BBB. A monoclonal antibody targeting a brain tumor needs to first enter the central nervous system either thru the BBB (for antibodies crossing the BBB from the vascular lumen across the BBB into the brain and central nervous system), be injected directly into the tumor (convection enhanced therapy), or be directly injected intrathecally (in spinal fluid). Other mechanisms for entry into the CNS should be proposed such as retrograde thru muscle or nerves. Only after the Monoclonal antibody enters the CNS can it bind to the primary intracranial brain tumor (if the brain tumor metastasizes to the periphery, the antibody can bind the tumor without entering the CNS).

In an embodiment, mRNA is able be internalized into the cell when it is encapsulated in a liposome conjugated to anti-CD155 antibody or antigen binding fragment. Anti-CD155 antibody D171 binds the poliovirus receptor at amino acid residues 35-50 of the poliovirus receptor. In an embodiment, a humanized antibody against human CD155 is conjugated to a liposome containing antisense DNA or antisense RNA, or plasmid or genes with native or chemically modified residues. In another embodiment, the liposome contains mRNA with native or chemically modifies residues. The humanized antibody against the human CD155 and the conjugated liposome are capable of crossing the blood brain barrier and delivering the mRNA or nucleic acid therapeutic to the CD155 expressing cells.

The present disclosure includes a viral delivery of therapeutics including mRNA and genes via ligand conjugates where the ligand, such as a monoclonal antibody, binds to CD155 leading to internalization and subsequent release of therapeutics permitting function of the drug or mRNA/gene expression (mRNA/gene). D171 antibody conjugated to mRNA encapsulated in liposomes has been shown here to be internalizable and able to deliver the payload to CD155 expressing cells where the mRNA was expressed in tumor cells in vitro. This proof of concept lays the groundwork for delivery of nucleic acid therapeutics and other drugs to cells with humanized anti-CD155 antibody drug conjugates.

In an embodiment, the ligand can be 1) an antibody against CD155, 2) an antibody or antigen binding fragments that binds the CD155, a fusion protein that binds CD155 wherein one part binds the CD155 and the other part is a toxin such as diphtheria, 3) a antibody or antigen binding fragment conjugated to a therapeutic drug or prodrug such as a nucleic acids or genes where the antibody or antigen binding fragment binds the CD155. The therapeutic drug or prodrug such as doxorubicin, siRNA, antisense DNA or other antisense molecules, messenger RNA encoding proteins or enzymes or peptides or cytokines, Cas9 mRNA, Cas12a mRNA and guide RNA for CRISPR, or naked DNA genes or plasmids. The antibody or antigen binding fragment against CD155 can be conjugated to a mRNA encoding one of the following mRNA for a cytokine (a) mRNA encoding IL-2 and (b) mRNA encoding IL-7 and (c) mRNA encoding IL-12, (d) mRNA encoding IL-15, (e) mRNA encoding IL-21 (f) mRNA encoding IFN gamma and (g) mRNA encoding IFN alpha, and (i) mRNA encoding GM-CSF.

In an embodiment, the humanized anti-CD155 antibodies can be used to target neurons, astrocytes, regenerating muscle, and the spinal cord. Antibodies against CD155 or fragments or fusion constructs either alone or conjugated have preoperative, intraoperative or postoperative diagnostic roles in identifying the full extent of tumor or extent of tumor resection. In one embodiment, a patient with GBM is treated preoperatively with fluorescent labeled antibody against CD155 that crosses the blood brain barrier or is directly injected in to the tumor, and the contours of the antibody fluorescence guides the surgeon intraoperatively with regards tumor resection.

Soluble CD155 can act as an antidote to overdose of anti-CD155 Antibody conjugates by adding the soluble CD155 to bind anti-CD155 antibodies. Furthermore, in one embodiment, treatment of patients with antibody drug conjugates of anti-CD155 antibodies is preceded by first administering unconjugated anti-CD155 antibodies to block CD155 on normal cells. The subsequent addition of the anti-CD155 antibody drug conjugates will then be directed to tumors overexpressing CD155. Antibodies against CD155 or fragments or fusion construct either alone or conjugates have diagnostic applications to identify tumors in brain, the extent of tumors in the brain by imaging mechanisms such as PET scan, MRI, Nuclear scan, CT scan, Ultrasound, and other imaging modalities standard to the art.

IV. Conclusion

While the function of CD155 is not fully known, CD155 has been shown to bind TIGIT (T cell immunoreceptor with Ig and ITIM domains), CD226 (DNAM 1) and CD96. Soluble CD155, a prognostic tumor biomarker, is often secreted from CD155 positive tumors and may function in binding DNAM 1. Membranous CD155 and Soluble CD155 may function to suppress the immune system thus permitting CD155 positive tumors to grow. Blocking of Soluble CD155 or Membranous CD155 with Anti-CD155 antibodies can reverse the immunosuppression. Blocking of CD155 with anti-CD155 antibodies can also block binding of CD155 to TIGIT thus diminishing the inhibitory signal conveyed by CD155-TIGIT binding. As such, CD155 is a novel checkpoint and CD155 modulation with anti-CD155 antibodies provides a novel pathway to treating cancer using multiple mechanisms of action.

While CD155 is found at lower levels in normal tissues such as muscle and kidney, CD155 is overexpressed on many different cancers making CD155 a novel yet common target for the treatment of wide variety of malignancies. Likewise, as described in this invention, the monoclonal antibodies of this invention bound not only CD155 but also Nectin 4, another tumor marker. The monoclonal antibodies in this invention were shown for the first time to bind Nectin 4. The monoclonal antibodies D171 and AB825 (Ab825 and AB825 are interchangeably used in this specification and Figures and Claims) which are related to the humanized antibodies of this invention were never before shown to bind Nectin 4. Nectin 4 has recently been shown to bind TIGIT. In one embodiment, the antibodies of this invention will block the binding of both Nectin 4 and PVR with TIGIT thereby blocking the inhibitory signal to immune cells such as T Cells. In another embodiment, the antibodies or antigen binding fragments against CD155 is administered to a human for the treatment of cancer in combination with an additional drug, cell therapy or an immunomodulator comprised of an antibody against a checkpoint molecule. The antibodies or antigen binding fragments against CD155 is administered to a human in combination with an additional immunomodulator comprised of an antibody against an immune checkpoint molecule selected from then group consisting of CTLA 4, PD1, PDL1, CD112R, OX40, TIGIT, NKG2A, CEACAM 1, B7H3, B7-H4, VISTA, LAG3, CD137, KIR, TIM1, TIM3, LAIR 1, HVEM, BTLA, CD160, CD200, CD200R and A2r.

In an embodiment, the anti-CD155 antibody or antigen binding fragments is fused to an antibody or antigen binding fragments that is known to cross the blood brain barrier such as the anti-transferrin receptor antibody or antigen binding fragments (or the FC 5 antibody or antigen binding fragments that crosses the blood brain barrier). The anti-CD155 antibody or antigen binding fragments can be coupled to the antibody (or antigen binding fragments) that crosses the blood brain barrier either chemically or thru recombinant techniques thus enabling the anti-CD155 antibody to cross the blood brain barrier. In another embodiment a bispecific antibody comprising the antibodies described in this invention binds CD155 (or Nectin 4) on tumors and CD3 on T cells. In another embodiment a bispecific antibody comprising one or more of the antibodies described in this invention binds CD155 (or Nectin 4) on tumors and another part of the bispecific antibody binds a receptor on NK cells (i.e., CD16, SLAM receptor, NKp46, NKp44 or NKp30 on NK cells). In an embodiment, the anti-CD155 antibody or antigen binding fragments is fused to an antibody or antigen binding fragments that is known to cross the blood brain barrier such as the anti-transferrin receptor antibody or antigen binding fragments (or the FC 5 antibody or antigen binding fragments that crosses the blood brain barrier). The anti-CD155 antibody or antigen binding fragments can be coupled to the antibody (or antigen binding fragments) that crosses the blood brain barrier either chemically or thru recombinant techniques thus enabling the anti-CD155 antibody to cross the blood brain barrier. The antibodies of this invention bind and block the PVR (CD155). The humanized monoclonal antibodies of this invention may be used to treat patients exposed to the poliovirus by blocking the poliovirus receptor and preventing poliovirus from binding to the poliovirus receptor (PVR; CD155).

In one embodiment, the antibodies of this invention may also be administered to a mammal, including humans, to treat infections such as HIV by elevating the expression of DNAM 1 (CD226) on T cells. Likewise, in another embodiment, the antibodies of this invention may be used to treat sepsis by elevating the expression of DNAM 1 on T cells and Nk cells. It is conceivable that an overdose of the humanized antibodies against CD155 of this invention can be treated by administering soluble CD155 to bind the humanized antibodies and neutralize its effects. In another embodiment of this invention, the AB825, D171 or any of the humanized antibodies of binds to PVR (CD155) in vivo in animals expressing the human PVR. The human PVR can be an expressed transgene or the human PVR can be expressed on human cells such as U87 tumor cells implanted in mice. Prior to this work, Ab825 or any of the humanized antibodies of this invention were never injected in vivo in live animals. In another embodiment, Ab825 and the humanized antibodies against CD155 described in this invention have been shown to bind Vero cells from African Green Monkeys, thus these antibodies bind PVR (CD155) in nonhuman primates (FIG. 8).

The D171 antibody is an anti-CD155 antibody that was conjugated to liposome encapsulated mRNA and successfully delivered and expressed in human U87MG tumors. For the first time, it was shown that an anti-CD155 antibody (D171) is internalized and the liposomal mRNA conjugated to the D171 was internalized and was expressed. This work provided foundational support for making antibody drug conjugates of D171, Ab825 and the related humanized antibodies in this invention. The internalization of D171 and its ability to carry payload to a human tumor cells is also an embodiment of this invention. The uptake experiments with eGFP-RNA containing liposomes and fluorescein-RNA containing liposomes showed a clear superiority of anti-CD155 antibody conjugation over all other tested conjugates, and this only at the low concentrations that were allowed testing by the low quantity available. Moreover, these results were obtained with both types of CD155 antibodies in the conjugates, human specific or mouse specific, which thus reinforces the robustness of this result.

The mRNA was expressed after internalization in U87 tumors. In another experiment more than 80% of the U87 cells were labeled with fluorescein upon administration of liposome encapsulated fluorescein labeled mRNA conjugated to D171 antibody. This work for the first time provided foundational support for making antibody drug conjugates of D171, Ab825 and other related antibodies such as the humanized antibodies in this invention. The internalizability of D171, Ab825 and the humanized antibodies in this invention and its ability to carry payload to a human tumors is also an embodiment of this invention. Beside these results, only the anti-IL-13 alpha 2 conjugated liposomes showed mild but repetitive uptake in the different experiments, this in the mouse version (in GL261) or human version (in U87MG). RNA fluorescent labelling with fluorescein could be replaced by another more robust fluorophore which could be less sensitive to fluorophore bleaching for High Content Imaging image acquisition. The uptake of functional liposomes was explored in complete medium (containing 10% serum), which is a condition closer to in vivo conditions. 10, 50 or 100 ng/well of eGFP encoding RNA in functionalized liposomes were applied on 3 densities of GL261 or U87MGcells. Anti-CD155 antibodies conjugates could only be tested at 10 ng RNA/well because a very of the quantity available. The results show a repeated increase in cellular fluorescence after application of 10 ng RNA/well of Anti-CD155 antibodies conjugated liposomes at all cellular densities tested, for the mouse and human antibodies conjugates.

Humanization of Anti-CD155 Antibody

Ab825 is an antibody that shares sequences with the anti-CD155 antibody, D171. D171 was first described in 1985 by Nobis et al (J General Virology). Sequencing data showed that the heavy chain variable region (VH) of D171 antibody has more than 90% of the sequence identical to the heavy chain variable region (VH) sequence of Ab825. The light chain variable region (VL) of the D171 antibody and the CDRs of D171 also have significant overlap in sequence with Ab825. Given such a high degree of homology in the sequence of D171 and Ab825, there was no need humanize both antibodies separately. The Ab825 sequence was humanized by removing potentially immunogenic sequences. Ab825 was also analyzed for potential deamidation and isomerization sites, three of which were within the CDRs of Ab825. In addition to humanization, the potentially unstable sites were mutated and the panel of antibodies were then tested for binding properties.

The humanized anti-CD155 antibodies with the most optimal binding properties were than tested with cytokine release assay for risk of infusion reaction, Episcreen DC T cell assay for proliferative response, off target and on target binding with a panel of over 5000 known membrane receptors and epitope mapping of the binding site in PVR. The antibodies were also selected based on the ability to bind monkey CD155 (african green monkey-Vero cells). A less immunogenic sequence for humans was inserted in place of the immunogenic sequence. The antibodies were first mutated in the framework region and the variants were tested for binding and stability. The ability of the antibody to bind to the PVR receptor was assessed. The binding to the PVR receptor was maintained or improved or worsened in the numerous variants. In an embodiment, software is used to identify potentially immunogenic sequences to be removed.

There can still be bad immunogenic responses after removing the sequences identified in the software. Even after humanization, the various mutations have unpredictable impact in the binding or immunogenicity of the humanized antibody. Ab825 sequences were analyzed for immunogenicity and CDR instabilities/liabilities (such as aspartate isomerization site or a high or medium risk deamidation site), either of which may affect the conformation of CDRs and thus antigen binding (i.e binding to CD155). Promiscuous moderate and high affinity MHC class 2 binding sequences were also identified for humanization. Because of the unpredictable nature of altering labile sequences in the CDRs and impact of framework residues on binding to CD155, the humanized and liability reduced antibodies against CD155 that were generated were tested in CD155 positive HAP cells as well as CD155 knockout HAP cell lines.

As described above, the poliovirus receptor (PVR), also known as CD155, is overexpressed in many cancers including glioblastoma, malignant meningioma, malignant peripheral nerve sheath tumors, pancreatic cancer, lung cancer, and GI malignancies including colorectal cancer, breast cancer including triple negative (TNBC). The poliovirus receptor is also naturally found in healthy tissues, albeit with lower receptor densities, in cells such as motor neurons of the brain and spinal cord. There are known antibodies capable of binding to CD155 with varying degrees of efficiency. One example of such a known antibody is the murine antibody where the heavy and light chains were incorporated into a human IgG1 chimeric antibody designated herein as Ab825. Ab825 is derived from D171, a mouse antibody against human CD155. The heavy chain variable region (designated herein as VH0) and the light chain variable region (designated herein VK0) of Ab825 binds to the poliovirus receptor in human and non human primates. The heavy chain variable region VH0 is disclosed as Sequence ID NO 1 and the light chain variable region VK0 is disclosed as Sequence ID NO 5. The complementarity determining regions (CDRs) of VH0, CDR1, CDR2, and CDR3 are disclosed as Sequence ID NO 2, Sequence ID NO 3, and Sequence ID NO 4, respectively. The CDRs of VK0, CDR1, CDR2 and CDR3 are disclosed as Sequence ID NO 6, Sequence ID NO 7, and Sequence ID NO 8, respectively. The amino acid sequences listed in SEQ ID 1 to SEQ ID 31 and the CDR definitions and protein sequencing are according to Kabat.

One aspect of the present invention involves modifying and humanizing this heavy chain variable (VH) region and light chain variable (VK) region in order to make the antibody more stable and to minimize the immunogenicity and toxicity when the antibodies are used for therapeutic and diagnostic purposes in living humans. To form such antibodies or antigen binding fragments, the designed variable region genes were cloned into vectors encoding a human IgG1 or IgG4 heavy chain constant domain and a human kappa light chain constant domain. Chimeric and humanized antibodies (including IgG4 S241P) were transiently expressed in CHO cells, purified by Protein A and tested for binding to the PVR using Biacore (Surface Plasmon Resonance).

Structural models of the Ab825 antibody variable regions were produced and analyzed in order to identify important constraining amino acids in the variable regions that were likely to be essential for the binding properties of the antibody. Based upon this structural analysis, a large preliminary set of sequence segments were identified that could be used to create Ab825 humanized variants. These segments were selected and analysed for in silica analysis of peptide binding to human MHC class II alleles and compared to known antibody sequence-related T cell epitopes. Sequence segments that were identified as significant nonhuman germline binders to human MHC class II or that scored significant hits in our analysis were discarded. This resulted in a reduced set of segments, and combinations of these were again analysed, as above, to ensure that the junctions between segments did not contain potential T cell epitopes. Selected sequence segments were assembled into complete variable region sequences that were devoid of significant T cell epitopes. Thermostability and Freeze thaw stability of the humanized antibodies were also determined.

Employing the above analysis, five variable region heavy chains (designated VH1 to VH5) and four variable regions light chains (designated VK1 to VK4) were identified as having enhanced binding properties. These regions are disclosed by the following sequence ID Nos:

| Sequence ID Number | Sequence Designation |
|---|---|
| SEQ ID NO. 9 | VH1 |
| SEQ ID NO. 10 | VH2 |
| SEQ ID NO. 11 | VH3 |
| SEQ ID NO. 12 | VH4 |
| SEQ ID NO. 13 | VH5 |
| SEQ ID NO. 14 | VK1 |
| SEQ ID NO. 15 | VK2 |
| SEQ ID NO. 16 | VK3 |
| SEQ ID NO. 17 | VK4 |

In one embodiment, the invention is an antibody or antigen binding fragments against the poliovirus receptor (CD155) of an IgG isotype. This antibody or antigen binding fragments will have a heavy chain variable region from any one of SEQ ID NOS. 1, 9, 10, 11, 12, or 13 with a CDR 1 of SEQ ID NO. 2 and a CDR 3 of SEQ ID NO. 4. The CDR2 will be SEQ ID NO. 3, but with one or more of the following modifications:

(1) the asparagine in the sixth position of CDR 2 is substituted with one of alanine, glutamic acid, lysine, glutamine, serine, or threonine; and/or (2) the aspartic acid in the eighth position of CDR 2 is substituted with one of glutamic acid, glycine, or arginine; and/or (3) the threonine in the ninth position of CDR 2 is substituted with one of glutamic acid or lysine.

The light chain variable region will be any one of SEQ ID NOS. 5, 14, 15, 16, or 17 with a CDR 1 of SEQ ID NO. 6 and a CDR 2 of SEQ ID NO. 7. The CDR3 will be SEQ ID NO. 8, but with the asparagine in the fourth position of CDR 3 being substituted with one of alanine, glutamic acid, glycine, lysine, glutamine, or serine.

In another embodiment, the antibody or antigen binding fragments against the poliovirus receptor (CD155) is an IgG isotype. However, in this embodiment, the heavy chain variable region and light chain variable region are defined in terms of their CDRs. For example, the heavy chain variable region will include the VH0 CDR 1 of SEQ ID NO. 2 and the VH0 CDR 3 of SEQ ID NO. 4. Again, the VH0 CDR2 will be SEQ ID NO. 3, but with one or more of the following modifications:

(1) the asparagine in the sixth position of CDR 2 is substituted with one of alanine, glutamic acid, lysine, glutamine, serine, or threonine; and/or (2) the aspartic acid in the eighth position of CDR 2 is substituted with one of glutamic acid, glycine, or arginine; and/or (3) the threonine in the ninth position of CDR 2 is substituted with one of glutamic acid or lysine.

The light chain variable region will have the VK0 CDR 1 of SEQ ID NO. 6 and the VK0 CDR 2 of SEQ ID NO. 7. The VK0 CDR3 will be SEQ ID NO. 8, but with the asparagine in the fourth position of CDR 3 being substituted with one of alanine, glutamic acid, glycine, lysine, glutamine, or serine. More preferred antibody embodiments were developed from particular combinations of the previously described heavy chain variable regions VH1-VH5 (SEQ ID NOS: 9-13) and light chain variable regions VK1-VK4 (SEQ ID NOS: 14-17). VH3 and VH4, together with VK2 and VK3 were deemed among the best variable heavy chain and light chain humanized variants based on the T cell epitope profile. VK or Vk are used interchangeably. VH and Vh are also used here interchangeably. To address the potential deamidation sites identified at VH N54 and VK N92 (using single letter amino acid symbols and the amino acid position number) and the potential isomerisation site associated with VH D56, a series of amino acid substitutions (six for the potential sequence liabilities at VH N54 and VK N92 and five for VH D56) were first introduced individually into the VH and VK regions by mutations in the VH0/VK0 chimeric antibody. The liability reduced substitutions in VH0/VK0 included mutations at VH N54Q, N54S, D56E and D56G together with VK N92E and N92Q and these variants of VH0/VK0 were tested for binding to the poliovirus receptor, and upon analysis of binding, were then selected to be incorporated in combination into certain preferred humanized variants of VH3/VK2, VH3/VK3 and VH4/VK3.

These modified VH and VK regions have the following sequence and designation:

| Sequence ID Number | Designation of Sequence |
|---|---|
| SEQ ID NO. 18 | VH3 N54Q D56E |
| SEQ ID NO. 19 | VK2 N92E |
| SEQ ID NO. 20 | VH3 N54S D56G |
| SEQ ID NO. 21 | VK2 N92Q |
| SEQ ID NO. 22 | VK3 N92E |
| SEQ ID NO. 23 | VK3 N92Q |
| SEQ ID NO. 24 | VH4 N54Q D56E |
| SEQ ID NO. 25 | VH4 N54S D56G |
| SEQ ID NO. 26 | VH4 N54S D56E |

| Sequence ID Number | Designation of Sequence |
|---|---|
| CDR sequences from the Heavy Chain Variable Region VH3 N54Q D56E | CDR 1 SEQ ID 2: EYTMH<br>CDR 2 SEQ ID 27: GIHPNQGETSYNQRFKG<br>CDR 3 SEQ ID 4: WTGDFDY |
| CDR sequences from the Light Chain Variable Region VK2 N92E | CDR 1 SEQ ID 6: KASQNVGTNVA<br>CDR 2 SEQ ID 7: SASYRYS<br>CDR3 SEQ ID 28: QQYESYPYT |
| CDR sequences from Heavy Chain Variable Region VH3 N54S D56G | CDR 1 SEQ ID 2: EYTMH<br>CDR 2 SEQ ID 29: GIHPNSGGTSYNQRFKG<br>CDR 3 SEQ ID 4: WTGDFDY |
| CDR sequences from Light Chain Variable Region VK2 N92Q | CDR 1SEQ ID 6: KASQNVGTNVA<br>CDR 2 SEQ ID 7: SASYRYS<br>CDR 3 SEQ ID 30: QQYQSYPYT |
| CDR sequences from Light Chain Variable Region VK3 N92E | CDR 1 SEQ ID 6: KASQNVGTNVA<br>CDR 2 SEQ ID 7: SASYRYS<br>CDR 3 SEQ ID 28: QQYESYPYT |
| CDR sequences from Light Chain Variable Region sequence VK3 N92Q | CDR 1 SEQ ID 6: KASQNVGTNVA<br>CDR 2 SEQ ID 7: SASYRYS<br>CDR 3 SEQ ID 30: QQYQSYPYT |
| CDR sequences of the Heavy Chain Variable Region VH4 N54Q D56E | CDR 1 SEQ ID 2: EYTMH<br>CDR 2 SEQ ID 27: GIHPNQGETSYNQRFKG<br>CDR 3 SEQ ID 4: WTGDFDY |
| CDR sequences of the Heavy Chain Variable Region VH4 N54S D56G | CDR 1 SEQ ID 2: EYTMH<br>CDR 2 SEQ ID 29: GIHPNSGGTSYNQRFKG<br>CDR 3 SEQ ID 4: WTGDFDY |
| CDR sequences of the Heavy Chain Variable Region VH4 N54S D56E | CDR 1 SEQ ID 2: EYTMH<br>CDR 2 SEQ ID 31: GIHPNSGETSYNQRFKG<br>CDR 3 SEQ ID 4: WTGDFDY |

Employing these VH and VK regions, nine preferred antibody (or antigen binding fragments) against the poliovirus receptor (CD155) were identified, having the following heavy chain variable region and light chain variable region, respectively:

(i) VH3 N54Q D56E [SEQ ID NO: 18] and VK2 N92E [SEQ ID NO: 19];

(ii) VH3 N54S D56G [SEQ ID NO: 20] and VK2 N92Q [SEQ ID NO: 21];

(iii) VH3 N54Q D56E [SEQ ID NO: 18] and VK3 N92E [SEQ ID NO: 22];

(iv) VH3 N54S D56G [SEQ ID NO: 20] and VK3 N92Q [SEQ ID NO: 23];

(v) VH4 N54Q D56E [SEQ ID NO: 24] and VK3 N92E [SEQ ID NO: 22];

(vi) VH4 N54S D56E [SEQ ID NO: 26] and VK3 N92E [SEQ ID NO: 22]:

(vii) VH4 N54S D56G [SEQ ID NO: 25] and VK3 N92E [SEQ ID NO: 22];

(viii) VH4 N54Q D56E [SEQ ID NO: 24] and VK3 N92Q [SEQ ID NO: 23];

(ix) VH4 N54S D56G [SEQ ID NO: 25] and VK3 N92Q [SEQ ID NO: 23].

Further testing of these nine antibodies suggested the most preferred binding profiles were found in the antibodies (ii) VH3 N54S D56G [SEQ ID NO: 20] and VK2 N92Q [SEQ ID NO: 21]; (iv) VH3 N54S D56G [SEQ ID NO: 20] and VK3 N92Q [SEQ ID NO: 23]; and (ix) VH4 N54S D56G [SEQ ID NO: 25] and VK3 N92Q [SEQ ID NO: 23].

In addition to the antibodies described above, the present invention is intended to encompass the novel heavy chain variable regions and light chain variable regions forming the antibodies. For example, the VH regions identified in SEQ ID NOS: 9-13 and 18, 20, and 24-26, as well as the VK regions identified in SEQ ID NOS: 14-17, 19, and 21-23, should each be considered a separate invention. The humanized antibodies in this invention were shown to bind not only CD155 but also Nectin 4 (PVRL4). The dual specificity of this antibody and antigen binding fragments described in this invention broaden the range of tumors that can be treated with the antibodies described in this invention. The humanized antibodies in this invention which are related to D171 and Ab825 have been shown for the first time to bind Nectin 4 in addition to binding PVR. D171 and AB825 or any of there variants were never previously shown to bind Nectin 4.

Another embodiment includes an antibody or antigen binding fragments against the poliovirus receptor (CD155) comprising:

(a) a heavy chain variable region selected from one of SEQ ID NO: 9, SEQ ID NO: 10, SEQ ID NO: 11, SEQ ID NO: 12, SEQ ID NO: 13, SEQ ID NO: 18, SEQ ID NO: 20, SEQ ID NO: 24, SEQ ID NO: 25 or SEQ ID NO: 26

(b) a light chain variable region selected from one of SEQ ID NO: 14, SEQ ID NO: 15, SEQ ID NO: 16, SEQ ID NO: 17, SEQ ID NO: 19, SEQ ID NO: 21, SEQ ID NO: 22 or SEQ ID NO: 23.

Below are some embodiments comprising the antibodies and antigen binding fragments above.

The antibody or antigen binding fragment above can be conjugated to a prodrug or a drug for the treatment of tumors expressing Nectin 4. The antibody or antigen binding fragment above can be conjugated to a prodrug or a drug for the treatment of tumors expressing CD155 (PVR). Another embodiment includes antibody drug conjugates above where the drug or prodrug is from one of the following: a nucleic acid, vedontin, a pyrrolobenzodiazepine, liposomal doxorubicin, a topoisomerase inhibitor, MMAE, MMAF, DM 1, paclitaxel, temozolomide, doxorubicin, deruxtecan, a radiosensitizing drug, tesirine, docaxtel and a PARP inhibitor. One embodiment includes antibodies or antigen binding fragments above where the antibody or antigen binding fragment binds CD155 and blocks the binding of CD155 to TIGIT. One embodiment includes antibodies or antigen binding fragments above where the antibody or antigen binding fragment binds Nectin 4 and blocks the binding of Nectin 4 to TIGIT. One embodiment includes the antibodies or antigen binding fragments above where the antibody or antigen binding fragments binds to CD155 in non-human primates. One embodiment includes the antibody or antigen binding fragment above where the antibodies or antigen binding fragments bind to Nectin 4. Another embodiment includes the antibody or antigen binding fragments above where the antibodies or antigen binding fragments binds CD155 (PVR) leading to elevation of DNAM 1 on at least one of the following (a) T cells and (b) NK cells. Another embodiment includes a bispecific antibody or antigen binding fragment comprised of the antibody or antigen binding fragment that binds either the poliovirus receptor or Nectin 4 and a second part of the bispecific antibody or antigen binding fragment that binds CD3 on T cells. Another embodiment includes the bispecific antibody or antigen binding fragments comprised of the antibody or antigen binding fragment above that binds either the poliovirus receptor or Nectin 4 and a second part of the bispecific antibody or antigen binding fragment that binds a receptor on NK cells. Another embodiment includes antibodies or antigen binding fragments of where the antibody or antigen binding fragments against CD155 is administered to a human and the antibody or antigen binding fragment binds to CD155 in the human and prevents poliovirus from binding to CD155.

Another embodiment includes antibodies or antigen binding fragments against the poliovirus receptor (CD155) where the antibody or antigen binding fragments against CD155 is administered to a human for the treatment of cancer in combination with an antibody against an immune checkpoint molecule selected from then group consisting of CTLA 4, PD1, PDL1, CD112R, OX40, TIGIT, NKG2A, CEACAM 1, B7H3, B7-H4, VISTA, LAG3, CD137, KIR, TIM 1, TIM3, LAIR 1, HVEM, BTLA, CD160, CD200, CD200R and A2r. Another embodiment includes antibodies against the poliovirus receptor (CF155) where the antibody against CD155 comprises an IgG4 isotype with a S241P hinge mutation or a S228P hinge mutation. Another embodiment includes antibodies or antigen binding fragments against the poliovirus receptor (CD155) where the antibody or antigen binding fragments against CD155 comprises a label from one of the following (a) I-124 (b) Gallium 68 or (c) Lutetium 177 (d) a contrast agent for CT scan (e) a contrast agent for MRI scan and (f) a diagnostic agent for PET scan. Another embodiment includes antibody or antigen binding fragment against the poliovirus receptor (CD155) where the antibodies or antigen binding fragments against CD155 is conjugated to a mRNA encoding one of the following mRNA for a cytokine or a mRNA for a gene editing enzyme (a) mRNA encoding IL-2 and (b) mRNA encoding IL-7 and (c) mRNA encoding IL-12, (d) mRNA encoding IL-15, (e) mRNA encoding IL-21 (f) mRNA encoding IFN gamma (g) mRNA encoding IFN alpha (h) mRNA encoding GM-CSF (i) mRNA encoding Cas9 (j) mRNA encoding Cas12a or (k) mRNA encoding Cas13. Another embodiment includes a CAR T cells or CAR NK cells comprising an antigen binding fragment above. Another embodiment includes antibodies or antigen binding fragments above where the antibody or antigen binding fragments against CD155 binds to CD155 expressed on a tumor and elicits an immune response against the tumor through ADCC or CDC. An embodiment includes the D171 antibody conjugate where the D171 antibody conjugate binds a tumor expressing CD155 and the D171 antibody conjugate is internalized by the tumor.

Another embodiment includes an antibody or antigen binding fragment with heavy chain variable region with SEQ ID 1 and a light chain variable region with SEQ ID 5 where the antibody or antigen binding fragment binds to Nectin 4. This antibody or antigen binding fragments of this invention where the antibody or antigen binding fragment blocks the binding of Nectin 4 to TIGIT. This antibody or antigen binding fragments may be conjugated to a prodrug or a drug for the treatment of tumors expressing Nectin 4. The antibody or antigen binding fragment comprising a heavy chain variable region of SEQ ID 1 and a light chain variable region with SEQ ID 5 where the antibody or antigen binding fragment binds PVR leading to elevation of DNAM 1 on T Cells or NK Cells.

EXAMPLES

Invention of Humanized Antibody and Antigen Binding Fragments Against CD155&Nectin 4

Example 1. Checkpoint Blockade

CD155 and Nectin 4 have each been described as ligands of TIGIT. Binding of CD155 with TIGIT or Binding of Nectin 4 with TIGIT leads to inhibition of T Cells or NK Cells, as TIGIT is expressed on immune cells. Blockade of CD155 or Nectin 4 with the antibodies of this invention will prevent either CD155 or Nectin 4 (or both) from binding TIGIT. PVR is a natural ligand of TIGIT (Alteber et al in Cancer Discovery in May 2021). PVR is also a natural ligand of CD226 and CD96. D171 has been shown to block PVR (CD155) from binding TIGIT (Yu et al in 2009 in Nature Immunology Volume 10 (9) Supplementary FIGS. 4*b* and 4*c*). Reches et al (Journal of Immunotherapy of Cancer in 2020) has shown that Nectin 4 is a ligand for TIGIT. D171 antibody also binds PVR and blocks PVR from binding CD96 (Meyer et al Journal of Biological Chemistry Vol 284 (4) pages 2235-2244 see also page 2242).

Example 2. T Cell and NK Cell Engager

The antibodies or antigen binding fragments of this invention that bind CD155 and Nectin 4 can be used to make bispecific antibodies or bispecific antigen binding fragments. Bispecific antibodies or bispecific antigen binding fragments is an embodiment of this invention where a bispecific molecule binds CD155 and CD3 (or Nectin 4 and CD3). Ma et al in the Journal of Cancer in 2019 Vol 10 page 5153 have produced bispecific antibodies targeting CD3 and CD155. These bispecifics were shown to have activity against bladder cancer. Further examples include bispecifics that bind of CD155 (or Nectin 4) and a receptor on an NK cell to engage immune cells to destroy tumors that express CD155 (or Nectin 4). The antibodies and antigen binding fragments disclosed here can be incorporated in bispecific antibodies.

Example 3. Antibody Drug Conjugates (ADC)

Antibody Drug Conjugates (ADC) are an embodiment of this invention where the antibodies described are conjugated to drugs such as Vedontin, Deruxtecan and Tesirine where these drugs are conjugated to the antibodies of this invention and delivered to tumors that express either CD155 or Nectin 4 (or both). ADCs targeting CD155 are internalizable with delivery of therapeutics. These ADCs against CD155 have multiple mechanisms of action given that the target receptors are also a checkpoint molecule. The Antibody Drug Conjugates can be conjugated through various linkers known in the art including but not limited to cathepsin sensitive peptide crosslinkers. The antibody or antigen binding fragments may be conjugated to at least one drug (Antibody Drug Conjugate), such as MMAE, MMAF, paclitaxel, temozolomide, doxorubicin (including liposomal doxorubicin), deruxtecan, topoisomerase inhibitors, radiosensitizing drugs, radiolabeled antibody or antigen binding fragments, Tesirine, any pyrrolobenzodiazepine (PBD), DM 1, Vedontin and docaxtel and PARP inhibitors such as rucaparib. The antibody or the antigen binding fragment comprising the heavy chain variable region with SEQ ID 1 and a light chain variable region with SEQ ID 5 was conjugated to a fluorophore and administered to a mammal where the antibody conjugate binds and accumulates in tumors that express CD155 in the mammal (FIG. 4).

Example 4. ADC

ADC with nucleic acid delivery including mRNA. Anti-CD155 conjugates of Liposomes encapsulating mRNA for reporter molecule EGFP with delivery and expression of mRNA in CD155 expressing cancers. The antibodies or antigen binding fragments can also be conjugated to one or more therapeutic nucleic acids being delivered via antibodies or antigen binding fragments, where the therapeutic nucleic acid is any one or more of silencing RNA, shRNA, long RNA, ribozyme, messenger RNA, a plasmid DNA, or non-plasmid double stranded DNA and short single stranded DNA and double stranded DNA. Antibody Drug Conjugates can also be prepared by conjugating antibodies or antigen binding fragments in this invention with mRNA (encapsulated in liposomes or complexed with polymers) where the mRNA encodes peptides, proteins (such as IL-12, IL-15 or IL-2) and enzymes (such as gene editing enzymes Cas9 or Cas12a and other Cas enzymes such as Cas13). The D171 antibody conjugate were formed where the D171 antibody conjugate binds a tumor expressing CD155 and the D171 antibody conjugate is internalized by the tumor (FIG. 2 and FIG. 3). mRNA payload can be conjugated to the anti-CD155 antibodies to deliver mRNA encoding polypeptides and proteins including vaccines.

Example 5. DNAM 1-CD155 Axis

DNAM 1 (CD226) elevation can be achieved by administering Anti-CD155 antibodies with blockade of CD155 (membranous CD155 or blockade of Soluble CD155). A DNAM 1-CD155 Axis has been described where the expression of CD155 on cell membranes or secreted as soluble CD155 downregulate DNAM 1 (CD226) expression. Therapeutic intervention with the humanized monoclonal antibodies against CD155 is an embodiment of this invention where the Anti-CD155 antibodies are administered to patients with Cancer or HIV infection (or other diseases where DNAM 1 (CD226) is downregulated). Blockade of membranous CD155 or soluble CD155 with the humanized anti-CD155 antibodies of this invention will increase the expression of DNAM 1 (CD226) on T cells and NK cells. Elevation of DNAM 1 will re-establish immunosurveillance mechanisms. Carlsten et al (Journal of Immunology in 2009 Volume 183 page 4921) have shown that CD155 tumors downregulate CD155 on NK cells. Seth et al in the Journal of Biological Chemistry in 2011 have shown that anti-CD155 antibodies upregulate CD226 (DNAM 1) in T cells. The antibodies or antigen binding fragments disclosed in this application against CD155 may be used in the treatment of sepsis.

Example 6. CAR T and CAR NK

CAR T and CAR NK cells. Chimeric Antigen Receptor T Cells and Chimeric Antigen Receptor NK Cells can be prepared with the humanized antigen binding fragments described in this invention. The CAR T Cells and CAR NK cells can be used to target cancers that overexpress either CD155 or Nectin 4 (or tumors that express both CD155 and Nectin 4). For example, a humanized antigen binding fragment comprised of a HCVR such as SEQ ID 25 and a LCVR such as SEQ ID 23 can be incorporated into a CAR T and CAR NK cells.

Example 7. ADCC and CDC

ADCC and CDC are mechanisms by which antibodies bind tumor cells and the effector cells then destroy the cancer cells that are coated with the antibody. The antibodies against CD155 can facilitate ADCC or CDC upon binding and coating the cancers cells. The Fc region of the anti-CD155 antibodies can be further optimized for ADCC or CDC.

Example 8. Theranostics

Antibodies or antigen binding fragments against CD155 described here can be conjugated to at least one marker compound such as the fluorophore, IR 800 Dye. The antibodies and antigen binding fragments can also easily be radiolabeled with radioactive labels such as I-124 or Gallium68 for diagnosis or Lutetium 177 for therapy. The antibodies or antigen binding fragments described in this disclosure can be conjugated to at least one marker compound such as the fluorophore, IR 800 Dye.

Example 9. IgG4 S241P Isotype

The antibodies or antigen binding fragments described herein may be of an IgG isotype such as IgG1 IgG2 or IgG4 as wells as IgE and IgM isotypes. In one embodiment the humanized antibody against CD155 comprises an IgG4 isotype with a S241P hinge mutation or a S228P hinge mutation.

Example 10. Passive Immunity to Block PVR

The antibodies disclosed here are related to D171 which is known to bind the poliovirus receptor (CD155) and block poliovirus from binding the poliovirus receptor (CD155) (Nobis et al 1985 in Journal of General Virology Vol 66 page 2563). The humanized antibodies disclosed here can block the poliovirus receptor and block poliovirus from binding the poliovirus receptor in a human. The antibodies of this invention can be administered to patients to provide passive immunity to susceptible individuals who have been exposed to the poliovirus.

Example 11. Epitope Mapping

Linear and 3D Epitope mapping of PVR and Nectin 4 with humanized monoclonal antibodies that bind CD155 and Nectin 4 will be performed using the peptide excision approach where the CD155 or Nectin 4 antigen affinity is captured with immobilized test monoclonal antibodies. Limited proteolysis on the immune complex with washing of the unbound peptide (GluC and LysC digestion). Elution of the affinity bound peptides are then analyzed with high resolution mass spectrometry. Identification of peptides by comparison of the antigen peptide profiles with and without the antibody is then analyzed.

Example 12. Humanization Ab825 and D171

A sequence analysis of Ab825 showed various sites with liabilities were identified. The Heavy Chain Variable Region (HCVR) of Ab825 (SEQ ID 1) has potential high affinity promiscuous MHC Class 2 anchor residue at position 18 (Valine) and position 64 (Phenylalanine). The Light Chain Variable Region (LCVR) of Ab825 (SEQ ID 5) has potential high affinity promiscuous MHC Class 2 anchor residue at position 2 (Isoleucine) and 53 (Tyrosine). The HCVR of Ab825 (SEQ ID 1) also has potential PI moderate affinity promiscuous MHC Class 2 anchor residue at positions 32 (Tyrosine), position 48 (Isoleucine) and position 93 (Valine). The LCVR of Ab825 (SEQ ID 5) also has potential PI moderate affinity promiscuous MHC Class 2 anchor residue at position 3 (Valine), position 4 (Methionine), position 29 (Valine), position 47 (Leucine). Humanization of the heavy chain variable region and the light chain variable region of D171 or Ab825 has not previously been described or taught prior to this invention. Furthermore the stabilization of the potential deamidation sites and potential isomerization sites of Ab825 in the CDRs with mutations that stabilize the anti-CD155 antibody or antigen binding fragment is a critical part of this invention. Mutations in the CDRs are likely to impact binding and in fact many of the humanized variants tested with mutations in N54 and D56 mutations in the Heavy Chain Variable Region (HCVR) and mutations in the N92 in the Light Chain Variable Region (LCVR) had significantly diminished binding as evidenced by EC 50 in Vero cells, Hap cells and U87 cells (FIG. 8). The N54S D56G in the HCVR and N92Q in the LCVR had the most optimal binding properties and these mutations were within the CDR sequences of the HCVR and LCVR. The VH (Asn) 54 position of SEQ ID 1 which was identified as susceptible to deamidation can be mutated with the amino acids Alanine, Glutamate, Lysine, Glutamine, Serine and Threonine among others. The VH Asp56 of SEQ ID 1 which was identified as susceptible to isomerization can be mutated with amino acids Glutamate, Arginine or Threonine among others and the VH T 57 of SEQ ID 1 can be mutated with Glutamate or Lysine among others. The VKN92 of SEQ ID 5 was also identified as a potential deamidation site and can be mutated with amino acids Alanine, Glutamate, Glycine, Lysine, Glutamine or Serine among others.

The DC T cell assay showed that different variants of the humanized anti-CD155 antibodies had different degrees of immunogenicity. The data in FIG. 6 shows the percent frequency of proliferation responses from 50 donors on days 9, 10, and 11. The antibody with the HCVR VH4 N54S D56G (SEQ ID 25) and LCVR VK3 N92Q (SEQ ID 23) was the least immunogenic with lowest frequency of proliferation and lowest mean Stimulation Index (SI), even lower immunogenicity than observed for FDA-approved Herceptin® (trastuzumab). Cytokine Release Assay also showed that the antibody with the HCVR VH4 N54S D56G (SEQ ID 25) and LCVR Vk3 N92Q (SEQ ID 23) had the lowest risk of infusion reaction with a profile that was similar to control Erbitux. The antibody with the HCVR VH4 N54S D56G (SEQ ID 25) and LCVR Vk3 N92Q (SEQ ID 23) also has a much lower risk of infusion reaction than Ab825 (VH0/ Vk0) on cytokine release assay. Furthermore, the humanized variants were found to bind PVR and Nectin 4 when tested against over 5000 cell membrane receptors (FIG. 7). Ab825 and the humanized variants of Ab825 disclosed here were never known to bind Nectin 4 prior to this invention. Based on the results, humanized Ab825, D171, and Ab825 are expected to bind Nectin 4. Furthermore the lead humanized monoclonal antibodies against CD155 had sub nM dissociation constants thus confirming high affinity. The monoclonal antibody defined by SEQ ID 23 (LCVR) and SEQ ID 25 (HCVR) with a IgG4 (S241P) had a Kd=0.3 nM on surface plasmon resonance.

Example 13. Testing in Humanized Mice

Transiently humanized mice will be implanted with human tumors (with luciferase) that express CD155 and the humanized IgG4 S241P antibodies against CD155 will be given IV to the mice in combination with either alone in one set of mice or in combination with other checkpoint inhibitors and the size of tumors will be recorded with bioluminescence imaging. Likewise bispecific antibodies with humanized anti-CD155 antibodies and anti-CD3 antibodies will be tested in one group of mice. Another group of mice will be tested with ADCs prepared with humanized anti-CD155 mice and deruxtecan conjugated with a cathepsin sensitive peptide crosslinker. One control group of mice will be untreated mice. Transiently humanized mice are well known in the art where human tumors can be studied with human blood for a short time period.

Likewise, the invention contemplates not only the antibodies and antigen binding fragments, but also DNA encoding the antibodies or antigen binding fragments, as well as any other polynucleotide or plasmid comprising a nucleotide sequence encoding the antibodies or antigen binding fragments. The invention also includes any cell line that produces any of the antibodies or antigen binding fragments disclosed in this application. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods described herein without departing from the concept spirit and scope of the invention which is further defined by the appended claims.

---

What is claimed is:

1. A monoclonal antibody or antigen binding fragment against the poliovirus receptor (CD155) comprising:
   (a) a heavy chain variable region selected from the group consisting of SEQ ID NO: 18, SEQ ID NO: 20, SEQ ID NO: 24, SEQ ID NO: 25 or SEQ ID NO: 26 and
   (b) a light chain variable region selected from the group consisting of SEQ ID NO: 19, SEQ ID NO: 21, SEQ ID NO: 22 or SEQ ID NO: 23.

2. The monoclonal antibody or antigen binding fragment of claim 1 conjugated to a prodrug or a drug administered to a human for the treatment of tumors expressing CD155.

3. The monoclonal antibody or antigen binding fragment of claim 2, wherein the drug or prodrug is selected from one of the following: a nucleic acid, vedotin, a pyrrolobenzodiazepine, liposomal doxorubicin, a topoisomerase inhibitor, MMAE, MMAF, DM1, paclitaxel, temozolomide, doxorubicin, trastuzumab deruxtecan, a radiosensitizing drug, tesirine, docetaxel and a PARP inhibitor.

4. The monoclonal antibody or antigen binding fragment of claim 1, wherein the monoclonal antibody or antigen binding fragment binds CD155 and blocks the binding of CD155 to TIGIT.

5. The monoclonal antibody or antigen binding fragment of claim 1, wherein the monoclonal antibody or antigen binding fragment binds CD155 and blocks the binding of CD155 to CD96.

6. The monoclonal antibody or antigen binding fragment of claim 1 comprising a bispecific monoclonal antibody or antigen binding fragment including a first part that binds CD155 and a second part that binds at least one of the following: (a) CD3 on T cells and (b) NKp46 on NK cells.

7. The monoclonal antibody or antigen binding fragment of claim 1 comprising a bispecific monoclonal antibody or antigen binding fragment including a first part that binds CD155 and a second part that binds at least one of the following: (a) transferrin receptor 1 and (b) transferrin receptor 2.

8. The monoclonal antibody or antigen binding fragment of claim 1 comprising a bispecific monoclonal antibody or antigen binding fragment including a first part that binds the poliovirus receptor and a second part that binds Type 1 insulin-like growth factor receptor.

9. The monoclonal antibody or antigen binding fragment of claim 1 comprising a bispecific monoclonal antibody or antigen binding fragment including a first part that binds the poliovirus receptor and a second part comprising single domain antibody FC5.

10. The monoclonal antibody or antigen binding fragment of claim 1, wherein the monoclonal antibody or antigen binding fragment binds to CD155 in non-human primates.

11. The monoclonal antibody or antigen binding fragment of claim 1 with an IgG1 isotype where the monoclonal antibody or antigen binding fragment binds to CD155 expressed on a tumor and elicits an immune response against the tumor through ADCC or CDC.

12. The monoclonal antibody or antigen binding fragment of claim 1, wherein the monoclonal antibody or antigen binding fragment binds CD155 followed by an elevation of DNAM 1 on at least one of the following (a) T cells and (b) NK cells.

13. The monoclonal antibody or antigen binding fragment of claim 1, wherein the monoclonal antibody or antigen binding fragment against CD155 is administered to a human and the monoclonal antibody or antigen binding fragment binds to CD155 in the human and blocks poliovirus from binding to CD155.

14. The monoclonal antibody or antigen binding fragment of claim 1, wherein the monoclonal antibody or antigen binding fragment against CD155 is administered to a human for the treatment of cancer in combination with an antibody against an immune checkpoint molecule selected from the group consisting of CTLA-4, PD-1 PD-L1, CD112R, OX40, TIGIT, NKG2A, CEACAM1, B7-H3, B7-H4, VISTA, LAG-3, CD137, KIR, TIM-1, TIM-3, LAIR1, HVEM, BTLA, CD160, CD200, CD200R, and A2aR.

15. The monoclonal antibody or antigen binding fragment of claim 1, where in the monoclonal antibody or antigen binding fragment comprises an IgG4 isotype with a S241P hinge mutation.

16. The monoclonal antibody or antigen binding fragment of claim 1, wherein the monoclonal antibody or antigen binding fragment against CD155 comprises a label selected from one of the following: (a) 1-124, (b) Gallium 68, (c) Lutetium 177, (d) a contrast agent for CT scan, (e) a contrast agent for MRI scan and (f) a diagnostic agent for PET scan.

17. The monoclonal antibody or antigen binding fragment of claim 1, where the monoclonal antibody or antigen binding fragment against CD155 is conjugated to a mRNA encoding one of the following mRNA for a cytokine or a gene editing enzyme: (a) mRNA encoding IL-2, (b) mRNA encoding IL-7, (c) mRNA encoding IL-12, (d) mRNA encoding IL-15, (e) mRNA encoding IL-21, (f) mRNA encoding IFN gamma, (g) mRNA encoding IFN alpha, (h) mRNA encoding GM-CSF, (i) mRNA encoding Cas9, (j) mRNA encoding Cas12a and (k) mRNA encoding Cas13.

18. The monoclonal antibody or antigen binding fragment of claim 1 administered by at least one of the administration routes selected from the group consisting of intravenously, intra-arterially, intratumorally, intrathecally, intramuscularly, subcutaneously, intravascularly, intraperitoneally, and via convection-enhanced delivery.

19. A cell line that produces the monoclonal antibody or antigen binding fragment against the poliovirus receptor (CD155) comprised of a heavy chain variable region and a light chain variable region from the following:

- (a) a heavy chain variable region selected from the group consisting of SEQ ID NO: 9, SEQ ID NO: 10, SEQ ID NO: 11, SEQ ID NO: 12, SEQ ID NO: 13, SEQ ID NO: 18, SEQ ID NO: 20, SEQ ID NO: 24, SEQ ID NO: 25 or SEQ ID NO: 26 and
- (b) a light chain variable region selected from the group consisting of SEQ ID NO: 14, SEQ ID NO: 15, SEQ ID NO: 16, SEQ ID NO: 17, SEQ ID NO: 19, SEQ ID NO: 21, SEQ ID NO: 22 or SEQ ID NO: 23.

* * * * *